United States Patent
Hiraishi et al.

(10) Patent No.: US 10,494,362 B2
(45) Date of Patent: Dec. 3, 2019

(54) CITRIC ACID DERIVATIVE

(71) Applicants: ADABIO CO., LTD., Gunma (JP); OTSUKA PHARMACEUTICAL FACTORY, INC., Tokushima (JP)

(72) Inventors: Katsuya Hiraishi, Gunma (JP); Fumie Jimma, Gunma (JP); Hiroyuki Soma, Gunma (JP); Taro Adachi, Gunma (JP); Masakazu Adachi, Gunma (JP); Ippei Yamaoka, Tokushima (JP); Tomohiro Kagawa, Tokushima (JP)

(73) Assignees: ADABIO CO., LTD., Gunma (JP); OTSUKA PHARMACEUTICAL FACTORY, INC., Tokushima (JP)

( * ) Notice: Subject to any disclaimer, the term of this patent is extended or adjusted under 35 U.S.C. 154(b) by 0 days.

(21) Appl. No.: 15/770,300

(22) PCT Filed: Nov. 1, 2016

(86) PCT No.: PCT/JP2016/004789
§ 371 (c)(1),
(2) Date: Apr. 23, 2018

(87) PCT Pub. No.: WO2017/077707
PCT Pub. Date: May 11, 2017

(65) Prior Publication Data
US 2018/0334452 A1 Nov. 22, 2018

(30) Foreign Application Priority Data
Nov. 2, 2015 (JP) .................................. 2015-216000

(51) Int. Cl.
| | | |
|---|---|---|
| *C07D 405/04* | (2006.01) | |
| *C07D 207/12* | (2006.01) | |
| *C07D 307/20* | (2006.01) | |
| *A23L 33/105* | (2016.01) | |
| *A61K 31/4015* | (2006.01) | |
| *A61K 31/4025* | (2006.01) | |
| *A61K 31/341* | (2006.01) | |

(Continued)

(52) U.S. Cl.
CPC .......... *C07D 405/04* (2013.01); *A23L 33/105* (2016.08); *A61K 31/194* (2013.01); *A61K 31/197* (2013.01); *A61K 31/341* (2013.01); *A61K 31/4015* (2013.01); *A61K 31/4025* (2013.01); *C07C 231/02* (2013.01); *C07C 233/12* (2013.01); *C07C 235/12* (2013.01); *C07D 207/12* (2013.01); *C07D 207/416* (2013.01); *C07D 307/20* (2013.01); *A23V 2002/00* (2013.01)

(58) Field of Classification Search
None
See application file for complete search history.

(56) References Cited

U.S. PATENT DOCUMENTS 4,446,038 A * 5/1984 Schlicht ............... C10M 133/16
508/290
2016/0237213 A1 8/2016 Lansbergen et al.

FOREIGN PATENT DOCUMENTS

| CN | 101357118 A | 2/2009 |
| CN | 103960731 A | 8/2014 |

(Continued)

OTHER PUBLICATIONS

Khan et al., "Kinetics and Mechanism of Hydrolysis of Succinimide under Highly Alkaline Medium", J. Org. Chem., vol. 40, No. 12, pp. 1793-1794 (1975).
Stephenson et al., "Succinimide Formation from Aspartyl and Asparaginyl Peptides as a Model for the Spontaneous Degradation of Proteins", The Journal of Biological Chemistry, vol. 264, No. 11, pp. 6164-6170 (1989).

(Continued)

*Primary Examiner* — Kamal A Saeed
(74) *Attorney, Agent, or Firm* — Greenblum & Bernstein, P.L.C.

(57) ABSTRACT

Compounds (citric acid derivatives) represented by formulas (1) and (2) below are novel compounds having an inhibitory effect against liver disorder and can be used as liver disorder inhibitors and food additives (wherein $R^1$ represents a C1 to C3 alkyl group optionally having a carboxyl group or a hydroxyl group, and $R^2$ represents a hydrogen atom, or $R^1$ and $R^2$ optionally form a cyclic structure together to represent a C2 to C3 alkylene chain).

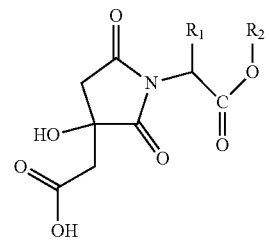

(1)

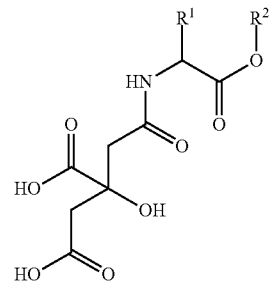

(2)

7 Claims, 8 Drawing Sheets

(51) Int. Cl.
*A61K 31/194* (2006.01)
*C07C 233/12* (2006.01)
*C07C 231/02* (2006.01)
*C07C 235/12* (2006.01)
*C07D 207/416* (2006.01)
*A61K 31/197* (2006.01)

(56) References Cited

FOREIGN PATENT DOCUMENTS

| | | | |
|---|---|---|---|
| JP | 2011-201841 | A | 10/2011 |
| JP | 4842624 | B2 | 12/2011 |
| JP | 2013-201997 | A | 10/2013 |
| JP | 5577129 | B2 | 8/2014 |
| WO | 2015/052342 | A1 | 4/2015 |
| WO | 2016/164437 | A1 | 10/2016 |

OTHER PUBLICATIONS

CAS Records from the CAS Registry File.
Yoshihiro Chuda et al., "Mumefural, Citric Acid Derivative Improving Blood Fluidity from Fruit-Juice Concentrate of Japanese Apricot (Prunus mume Sieb. et Zucc)", J. Agric. Food Chem., 47, pp. 828-831, 1999.
Yoshihiro Chuda et al., "Improvement in blood fluidity by fruit-juice concentrate of Japanese apricot", Journal of Hemorheology Research 1, pp. 65-67, 1998.
Nobuki Gato et al., "Mumefural-related compounds in fruit-juice concentrate of Japanese apricot and their ameliorating effect on blood fluidity through capillaries", Journal of Hemorheology Research 3, pp. 81-88, 2000.
Masaharu Miyake et al., "Isolation and identification of B-citryl-L-Glutamic acid from newborn rat brain", Biochimica et Biophysica Acta, pp. 656-666, vol. 544, 1978.
Stefan Schmelz et al., "AcsD catalyzes enantioselective citrate desymmetrization in siderophore biosynthesis", Nature Chemical Biology, vol. 5, No. 3, pp. 174-182, 2009.
Konetschny-Rapp et al., "Staphyloferrin A: a structurally new siderophore from staphylococci", European Journal of Biochemistry, vol. 191, pp. 65-74, 1990.
International Search Report from PCT/JP2016/004789, dated Dec. 6, 2016.
International Preliminary Report on Patentability from PCT/JP2016/004789, dated May 8, 2018.
Hokari et al., "Efficacy of MK615 for the treatment of patients with liver disorders," *World J Gastroenterol*, Aug. 21, 2012; 18(31): 4118-4126.
Adachi et al., "The 'prunus mume sieb. et zucc' (UME) is a rich natural source of novel anti-cancer substance," *International Journal of Food Properties*, 2007; 10: 375-384.

* cited by examiner

[Figure 1]
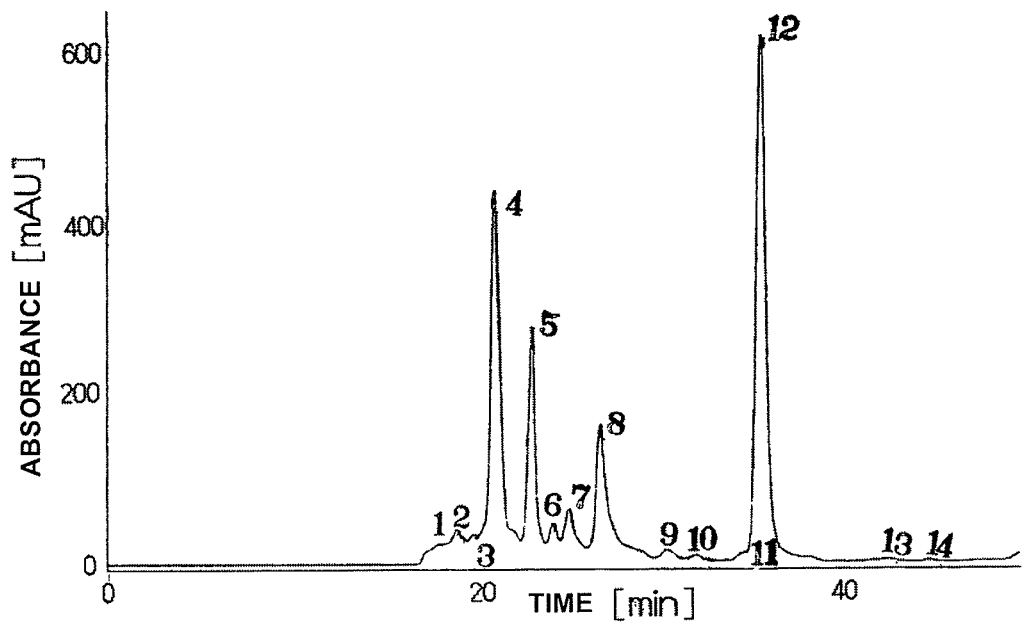
[Figure 2]
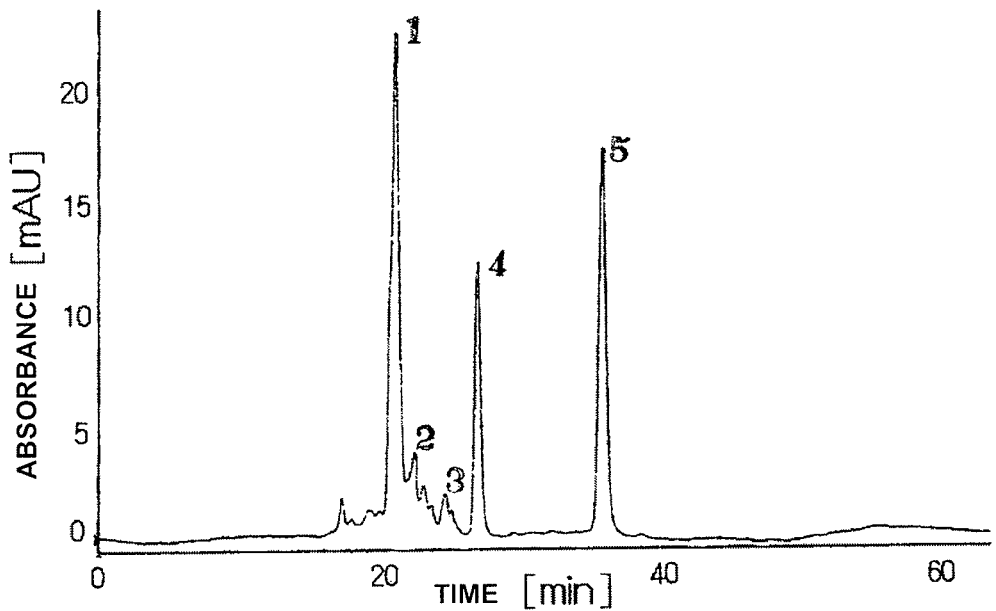

[Figure 3]
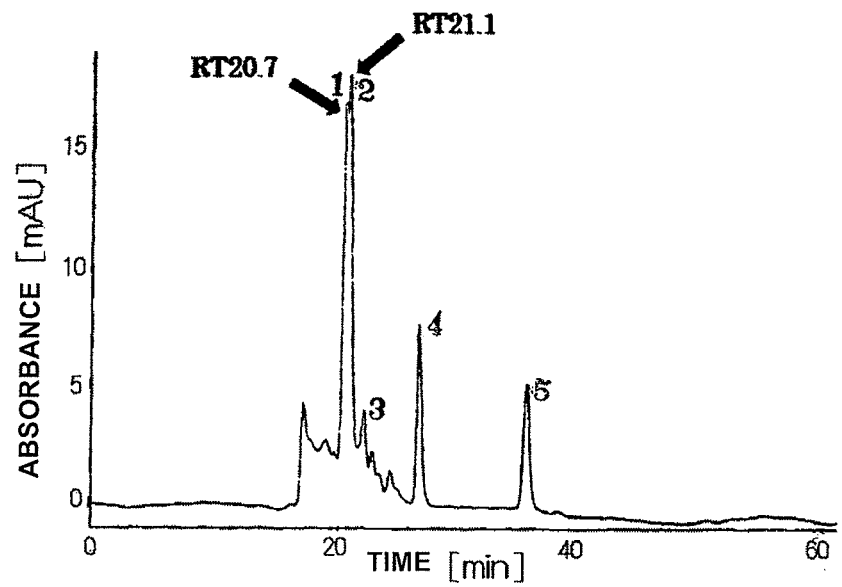
[Figure 4]
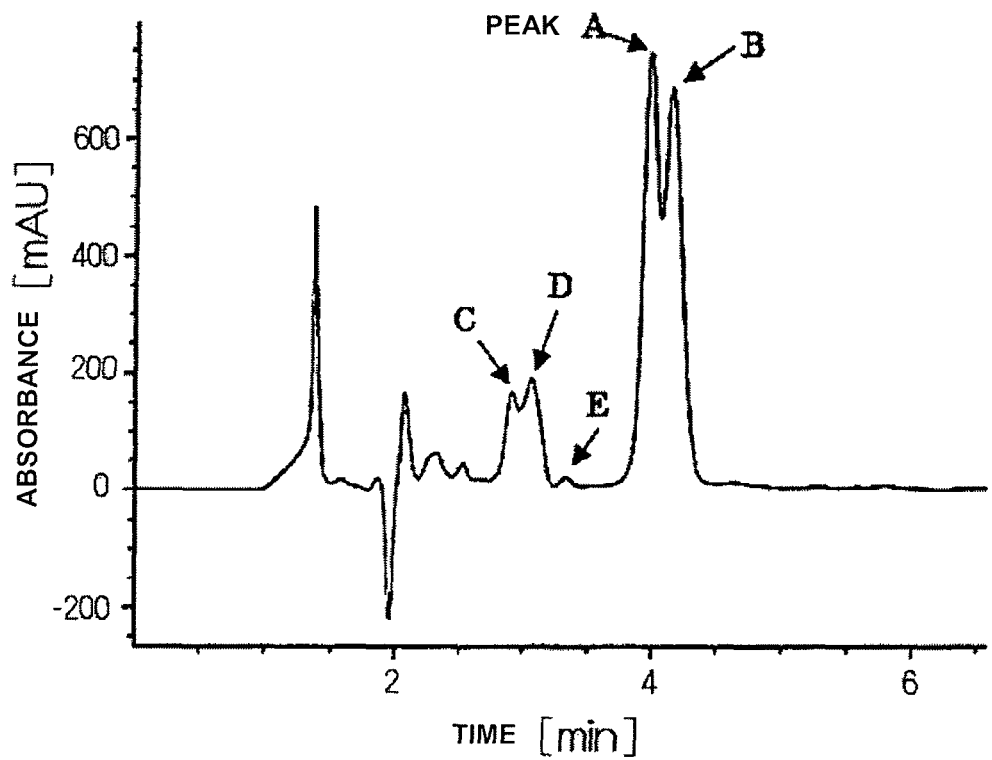

[Figure 5]
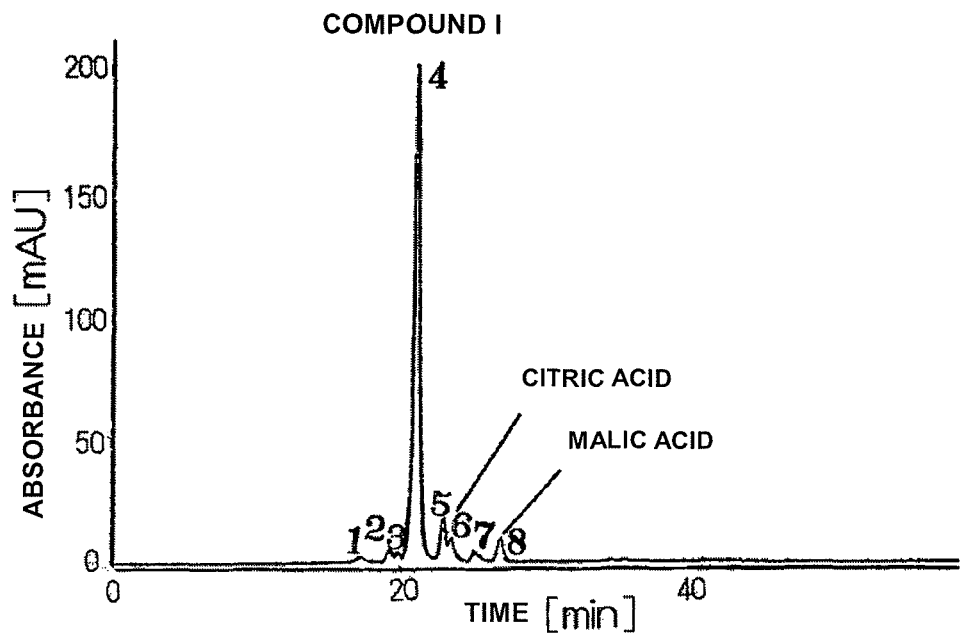
[Figure 6]
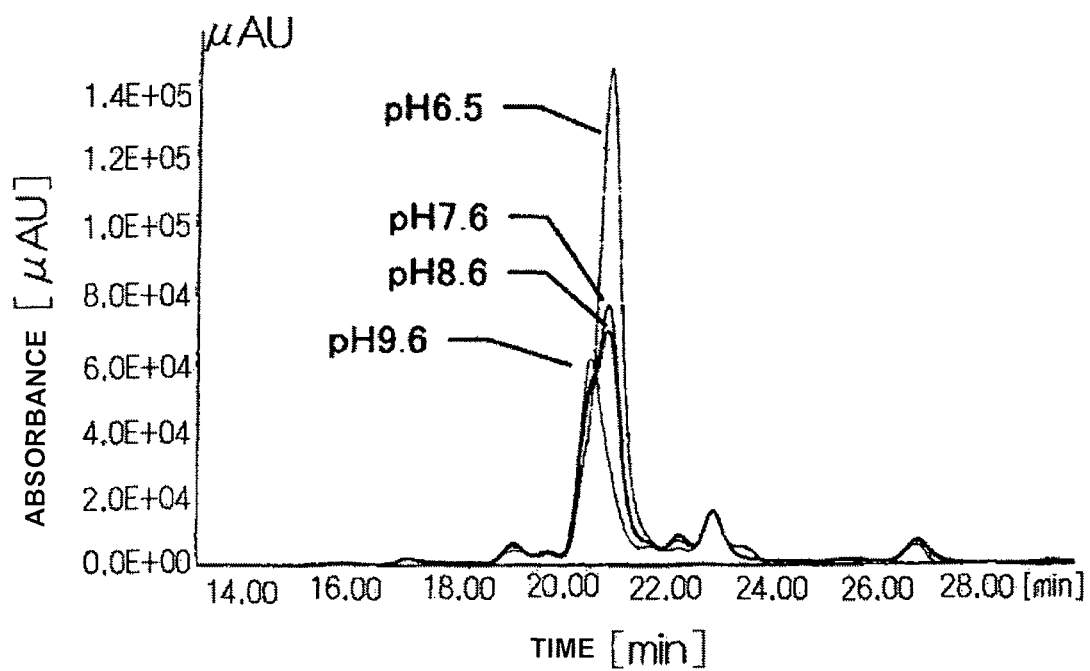

[Figure 7]
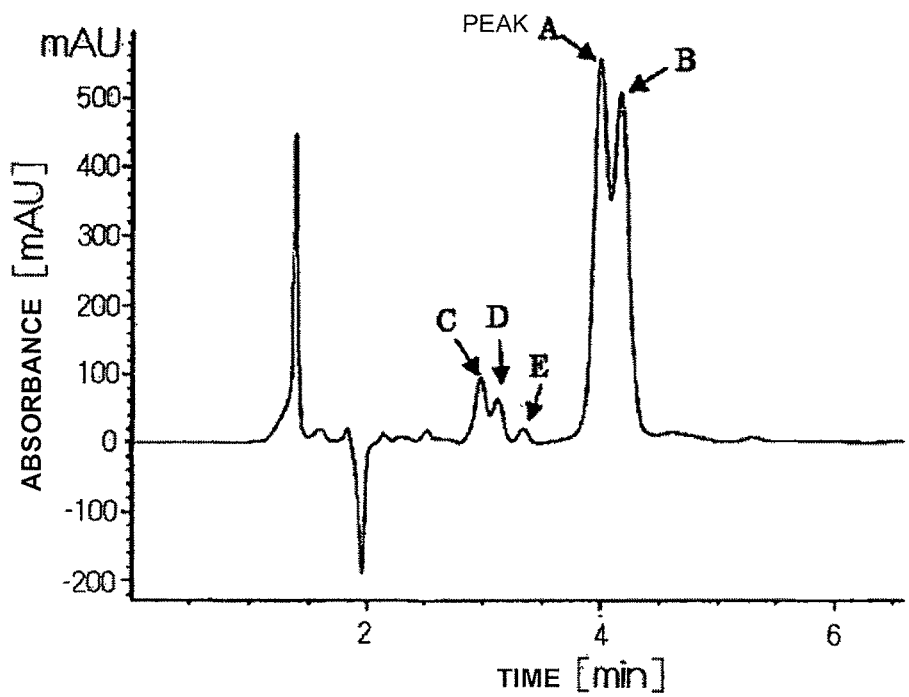
[Figure 8]
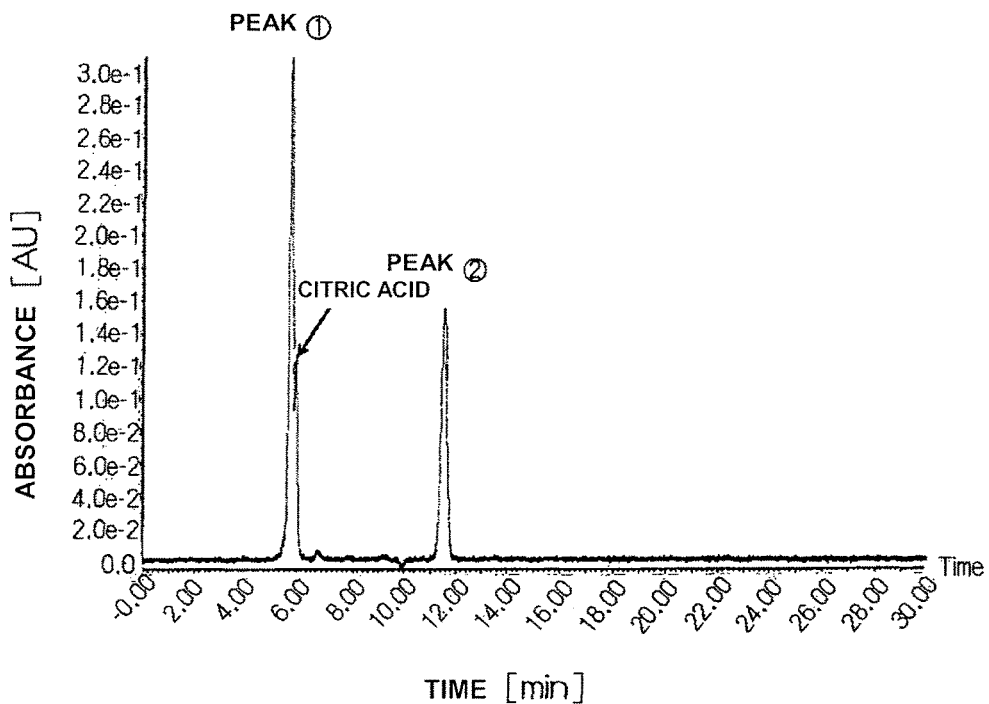

[Figure 9]
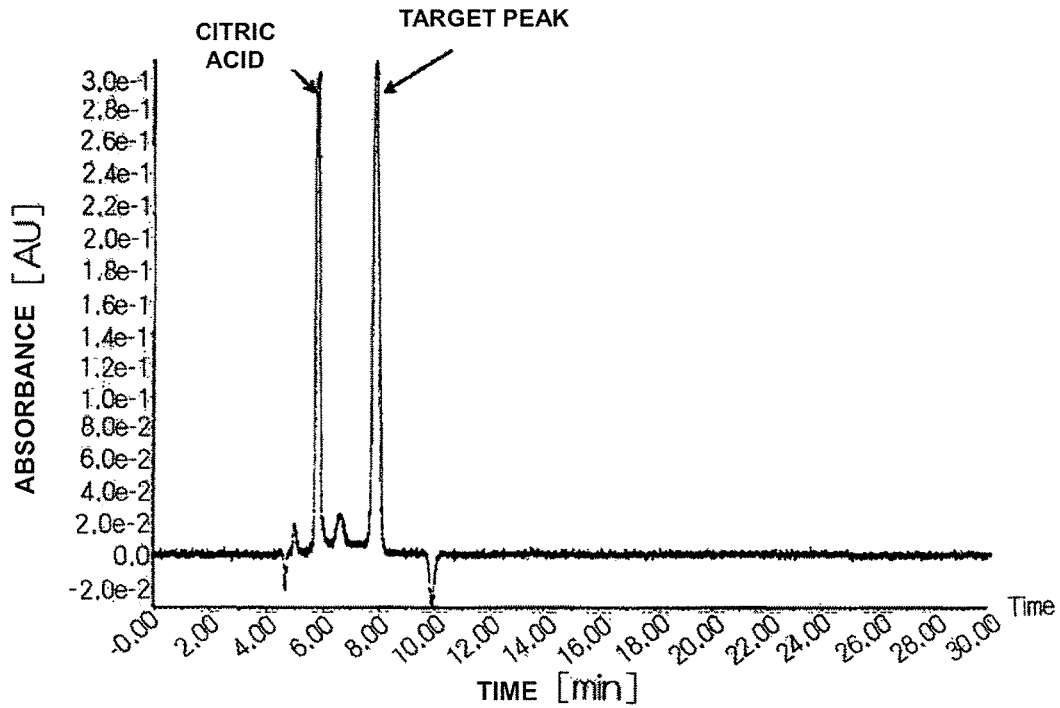
[Figure 10]
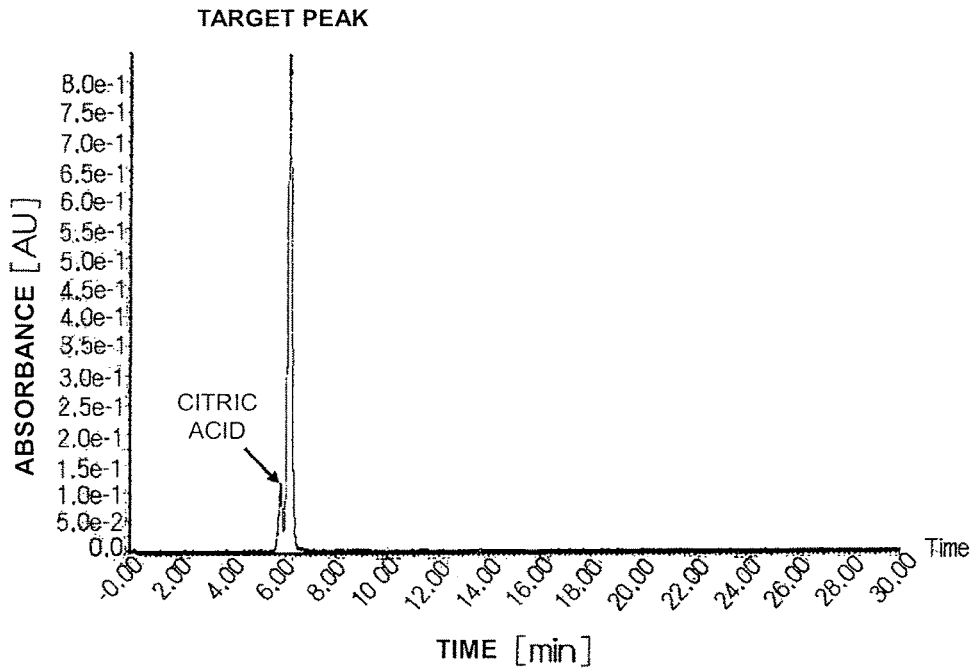

[Figure 11]
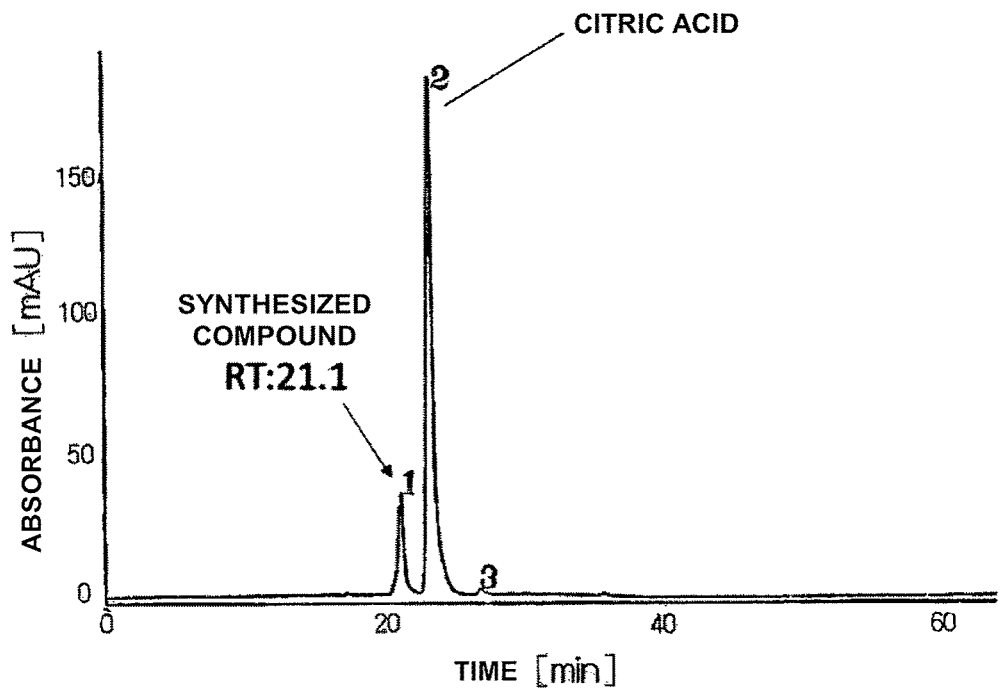
[Figure 12]
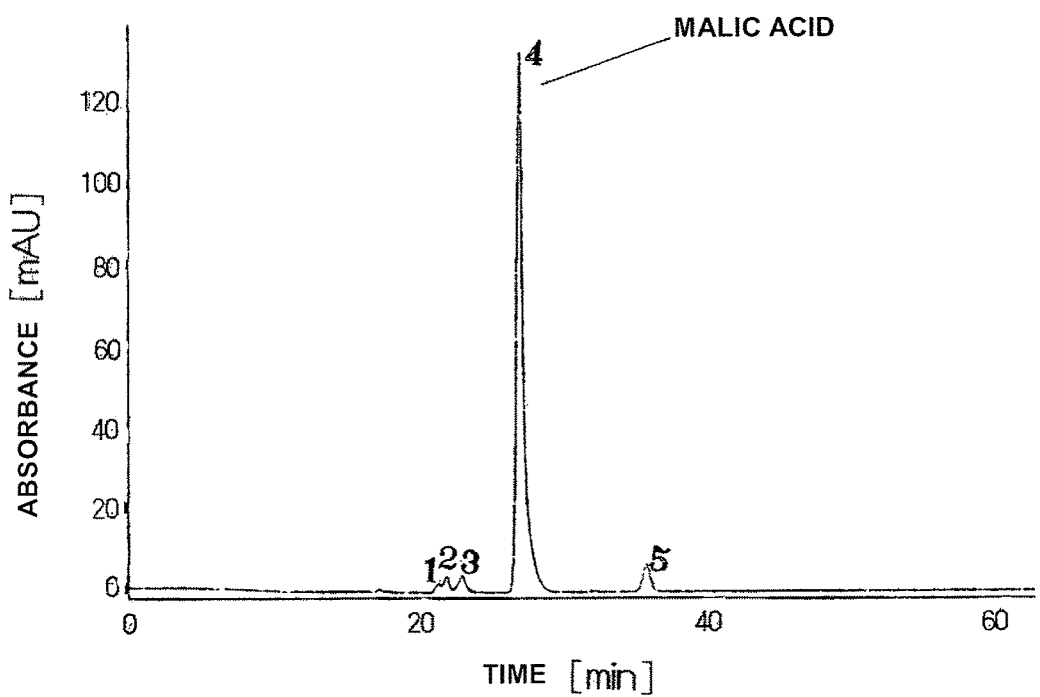

[Figure 13]
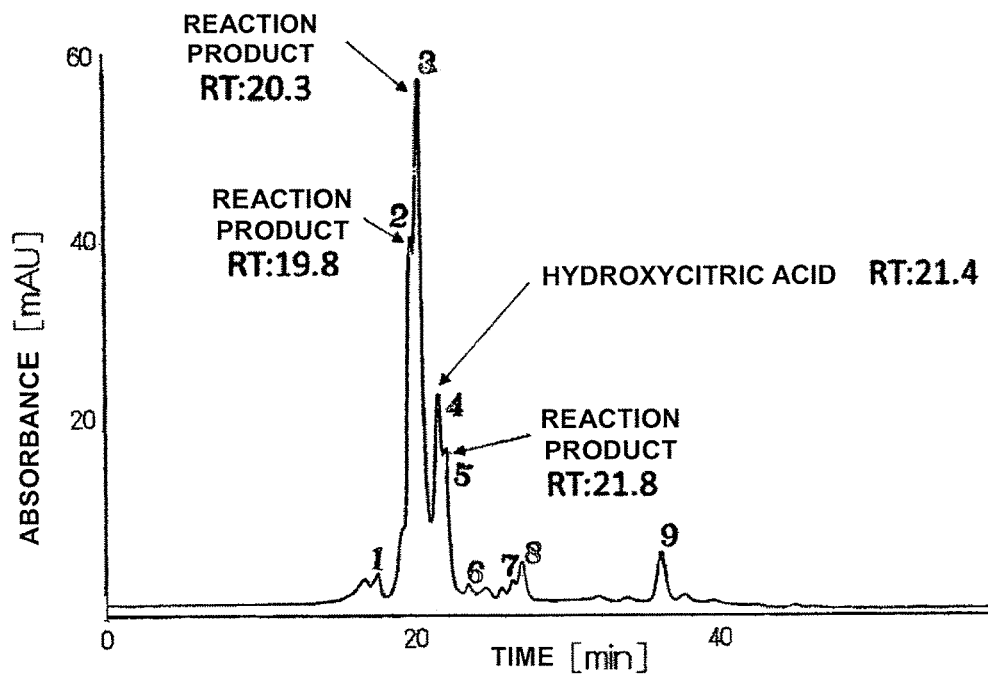
[Figure 14]
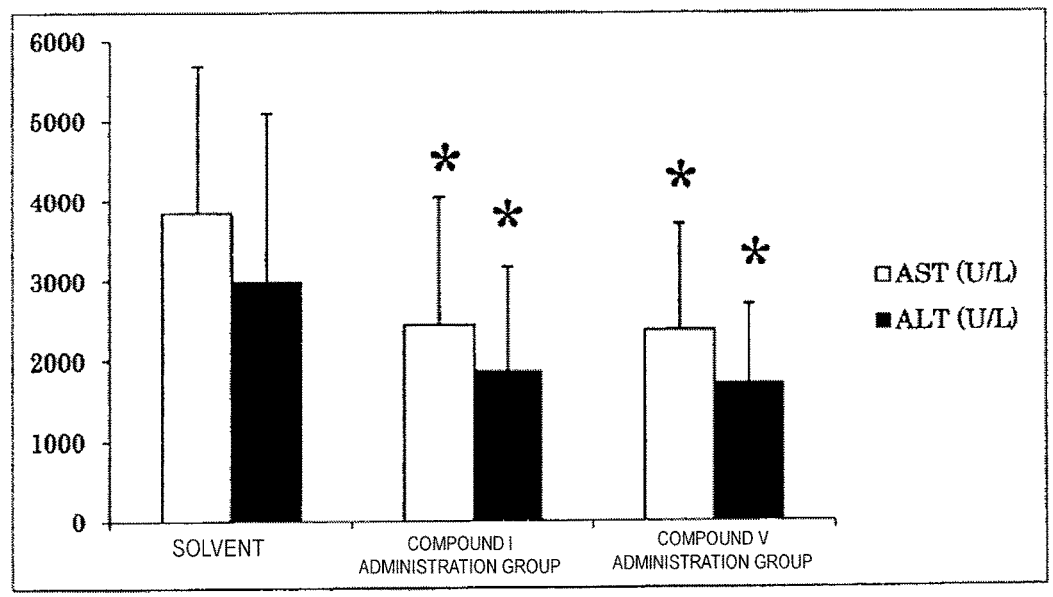

[Figure 15]
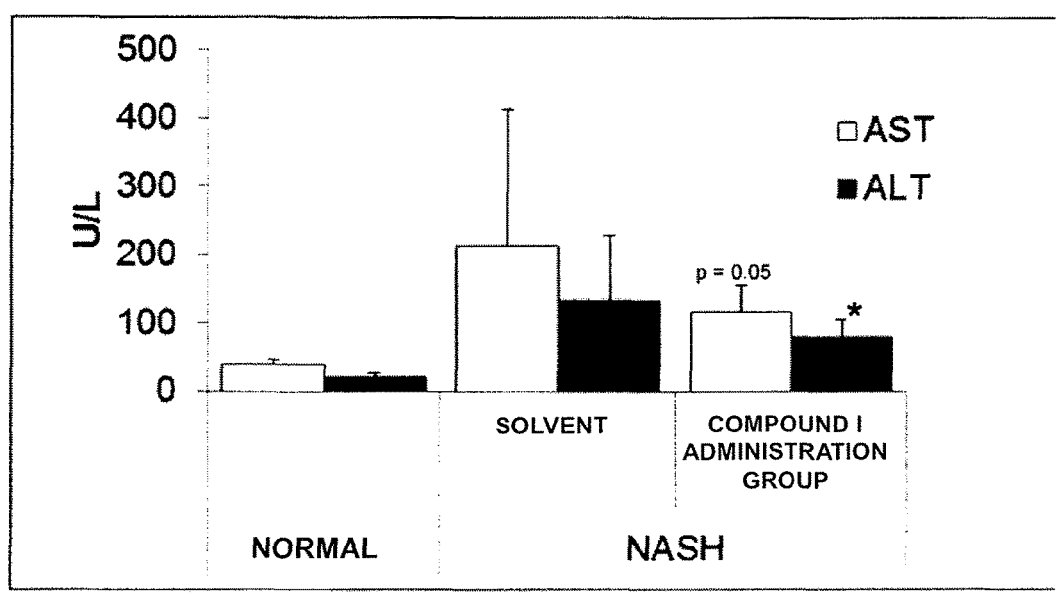

CITRIC ACID DERIVATIVE

TECHNICAL FIELD

The present invention relates to a novel citric acid derivative, and more specifically, to a citric acid derivative having an inhibitory effect against liver disorder.

BACKGROUND ART

Ume (Japanese apricot) (*Prunus mume*) belongs to the subgenus *Prunus* of the genus *Prunus* of the subfamily Amygdaloideae of the family Rosaceae and is eaten in the form of processed products of ume such as pickled ume, ume wine, and ume extract (ume flesh extract). Further, ume extract has advantageous effects such as sterilization, treatment from fatigue, and stomach protection action, and thus ume extract has been taken for health. Further, ume extract is known to have an effect of improving bloodstream (see Non-patent Documents 1 and 2). It is known that the effect of improving bloodstream is derived from Mumefural which is produced by heating an organic acid such as citric acid and malic acid contained in ume extract with sugar, and a related compound thereof (Non-patent Document 3).

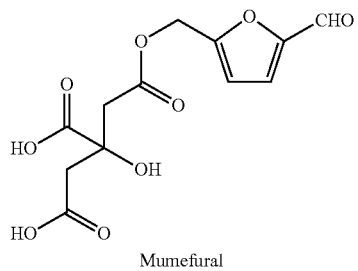 [SMILES: O=Cc1ccc(COC(=O)CC(O)(CC(=O)O)C(=O)O)o1]

Mumefural

Misatol (registered trademark) is commercially available as one of healthy food products containing ume extract, and Misatol is known to have an effect of inducing autophagy and an inhibitory effect against liver disorder in viral hepatitis patients (Patent Documents 1 and 2).

PRIOR ART DOCUMENTS

Patent Documents

Patent Document 1: Japanese Patent No. 4842624
Patent Document 2: Japanese Patent No. 5577129

Non Patent Documents

Non-patent Document 1: J. Agric. FoodChem., 1999, 47, 828-31
Non-patent Document 2: Journal of Hemorheology Research 1, 65-67, 1998
Non-patent Document 3: Journal of Hemorheology Research 3, 81-88, 2000

SUMMARY OF THE INVENTION

Object to be Solved by the Invention

An object of the present invention is to provide a compound having an inhibitory effect against liver disorder.

Means to Solve the Object

It has turned out that a compound in which two carboxyl groups bound to the 1-position carbon (or the 3-position carbon) and the 2-position carbon of a propane chain which is a carbon chain of citric acid (IUPAC name: 2-hydroxypropane-1,2,3-tricarboxylic acid) form an imide bond with an amino group of a specific amino acid, and an amide compound formed by reacting a carboxyl group bound to the 1-position carbon (or the 3-position carbon) of a propane chain derived from citric acid which is obtained by hydrolysis of the imide compound with amino acid are active substances having an inhibitory effect against liver disorder.

That is, the present invention relates to the following.

[1] A compound represented by formula (1) or (2):

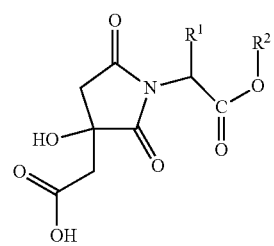

(1)

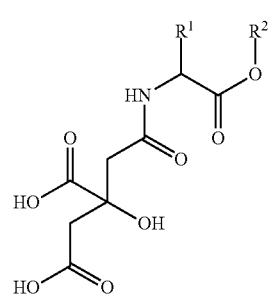

(2)

(wherein $R^1$ represents a C1 to C3 alkyl group optionally having a carboxyl group or a hydroxyl group, and $R^2$ represents a hydrogen atom, or $R^1$ and $R^2$ optionally form a cyclic structure together to represent a C2 to C3 alkylene chain).

[2] The compound according to [1], wherein the compound represented by formula (1) is represented by the following structures:

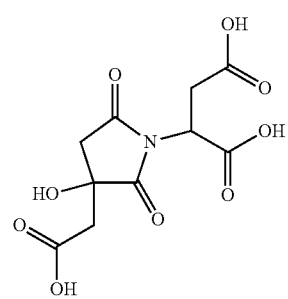

I

II

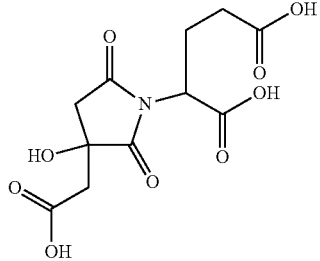

III

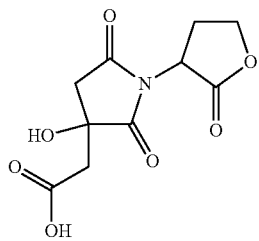

IV

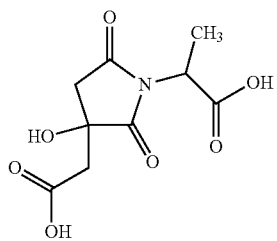

[3] The compound according to [1], wherein the compound represented by formula (2) is represented by the following structures:

V

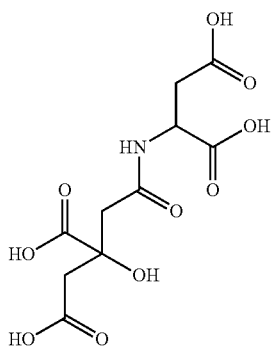

VI

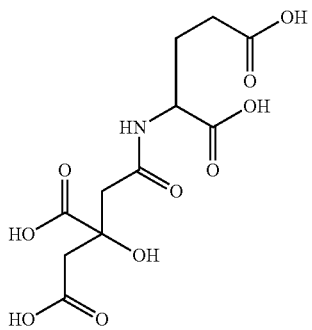

VII

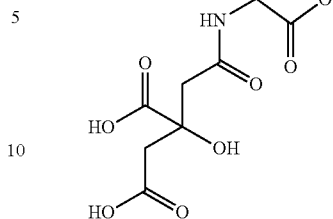

VIII

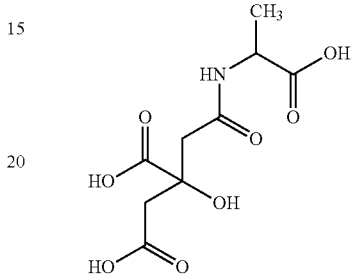

[4] A liver disorder inhibitor comprising: one or more compounds represented by formulas (1) and (2):

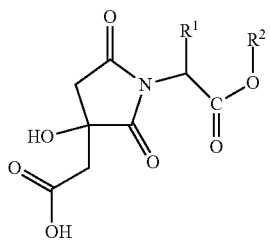

(1)

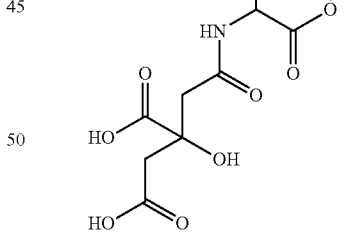

(2)

(wherein $R^1$ represents a C1 to C3 alkyl group optionally having a carboxyl group or a hydroxyl group, and $R^2$ represents a hydrogen atom, or $R^1$ and $R^2$ optionally form a cyclic structure together to represent a C2 to C3 alkylene chain).

[5] The liver disorder inhibitor according to [4], wherein the liver disorder is nonalcoholic steatohepatitis (NASH).

[6] A method for synthesizing a compound represented by formula (1), comprising: reacting by heating a mixture of citric acid and an amine compound represented by formula (3):

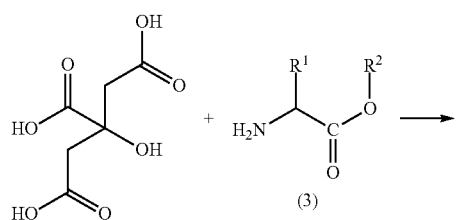

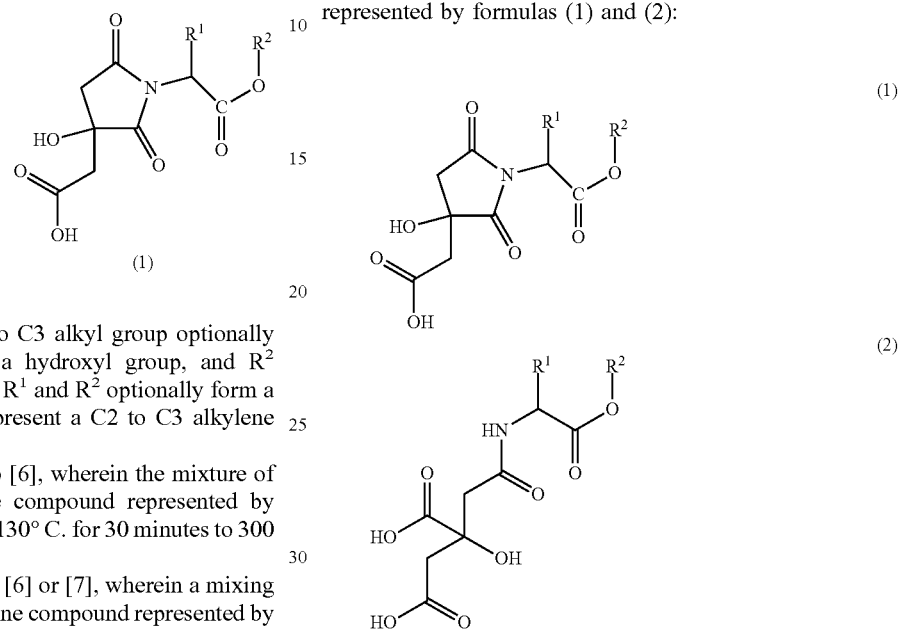

(wherein R¹ represents a C1 to C3 alkyl group optionally having a carboxyl group or a hydroxyl group, and $R^2$ represents a hydrogen atom, or $R^1$ and $R^2$ optionally form a cyclic structure together to represent a C2 to C3 alkylene chain).

[7] The method according to [6], wherein the mixture of the citric acid and the amine compound represented by formula (3) is reacted at 100 to 130° C. for 30 minutes to 300 minutes.

[8] The method according to [6] or [7], wherein a mixing ratio of the citric acid to the amine compound represented by formula (3) mixed (concentration of the citric acid:concentration of the amine compound represented by formula (3)) is 75:1 to 12:10.

[9] A method for conversion to a compound of formula (2), comprising: heating a compound represented by formula (1) in an aqueous solution to which an alkaline substance for generating hydroxide ions is added:

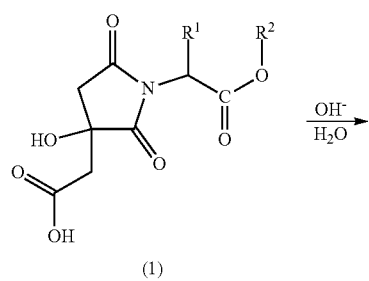

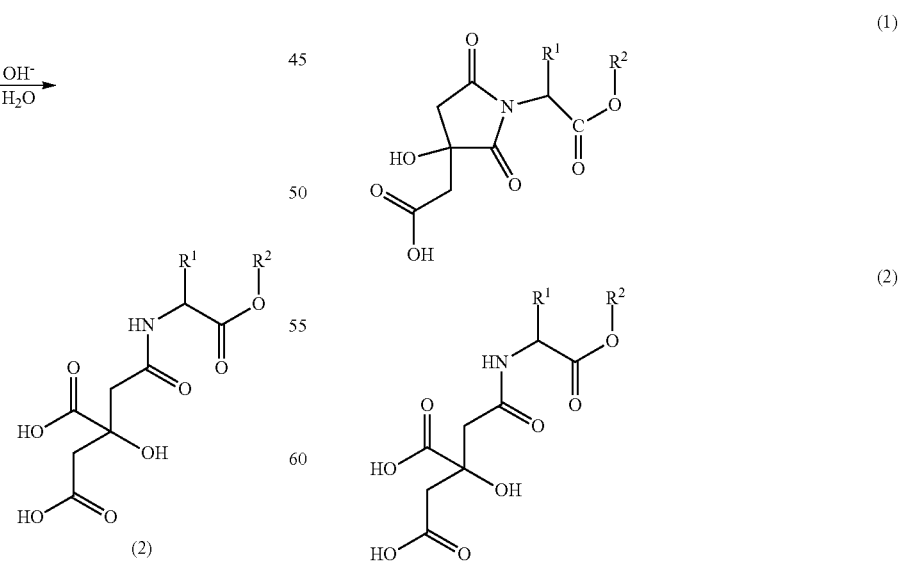

(wherein $R^1$ represents a C1 to C3 alkyl group optionally having a carboxyl group or a hydroxyl group and $R^2$ represents a hydrogen atom, or $R^1$ and $R^2$ optionally form a cyclic structure together to represent a C2 to C3 alkylene chain).

[10] The method according to [9], wherein the compound represented by formula (1) is allowed to react in an aqueous solution having a pH of 6.0 to 12.0 to which the alkaline substance for generating hydroxide ions is added, at 80 to 130° C. for 20 minutes to 240 minutes.

[11] A food product comprising one or more compounds represented by formulas (1) and (2):

(wherein $R^1$ represents a C1 to C3 alkyl group optionally having a carboxyl group or a hydroxyl group, and $R^2$ represents a hydrogen atom, or $R^1$ and $R^2$ optionally form a cyclic structure together to represent a C2 to C3 alkylene chain).

[12] A food additive comprising one or more compounds represented by formulas (1) and (2):

(wherein $R^1$ represents a C1 to C3 alkyl group optionally having a carboxyl group or a hydroxyl group, and $R^2$ represents a hydrogen atom, or R¹ and R² optionally form a cyclic structure together to represent a C2 to C3 alkylene chain).

Effect of the Invention

The compounds represented by formulas (1) and (2) have an inhibitory effect against liver disorder. Further, compounds I and V can be extracted, derived, and isolated also from ume extract.

BRIEF DESCRIPTION OF DRAWINGS

FIG. 1 is a graph showing the results of HPLC analysis of water-soluble components of ume extract.

FIG. 2 is a graph showing the results of HPLC analysis of a purified fraction containing a physiologically active component derived from ume extract.

FIG. 3 is a graph showing the results of HPLC analysis of a sample obtained by hydrolysis under alkaline conditions of the fraction containing the physiologically active component derived from ume extract.

FIG. 4 is a graph showing the results of HPLC analysis of the physiologically active components derived from ume extract and a hydrolysate thereof using high-resolution columns.

FIG. 5 is a graph showing the results of HPLC analysis indicating production of compound I by reaction of citric acid with L-aspartic acid.

FIG. 6 is a graph showing the results of HPLC analysis of a sample obtained by heating, under alkaline conditions, compound I synthesized from citric acid and L-aspartic acid.

FIG. 7 is a graph showing the results of HPLC analysis of compound I synthesized and a hydrolysate thereof using high-resolution columns.

FIG. 8 is a graph showing the results of HPLC analysis indicating production of compound II by reaction of citric acid with L-glutamic acid.

FIG. 9 is a graph showing the results of HPLC analysis indicating production of compound III.

FIG. 10 is a graph showing the results of HPLC analysis indicating production of compound IV.

FIG. 11 is a graph showing the results of HPLC analysis of a reaction solution of citric acid with aspartic acid.

FIG. 12 is a graph showing the results of HPLC analysis of a reaction solution of malic acid with aspartic acid.

FIG. 13 is a graph showing the results of HPLC analysis of a reaction solution of hydroxycitric acid with aspartic acid and asparagine.

FIG. 14 is a graph showing changes in ALT value and AST value of rats upon taking compounds I and V. In the figure, in each group, the bar graph on the left side shows AST, and the bar graph on the right side shows ALT.

FIG. 15 is a graph showing changes in ALT value and AST value of NASH model mice upon taking compound I. In the figure, in each group, the bar graph on the left side shows AST, and the bar graph on the right side shows ALT.

MODE OF CARRYING OUT THE INVENTION (Compounds)

The compounds of the present invention are compounds represented by formulas (1) and (2) below.

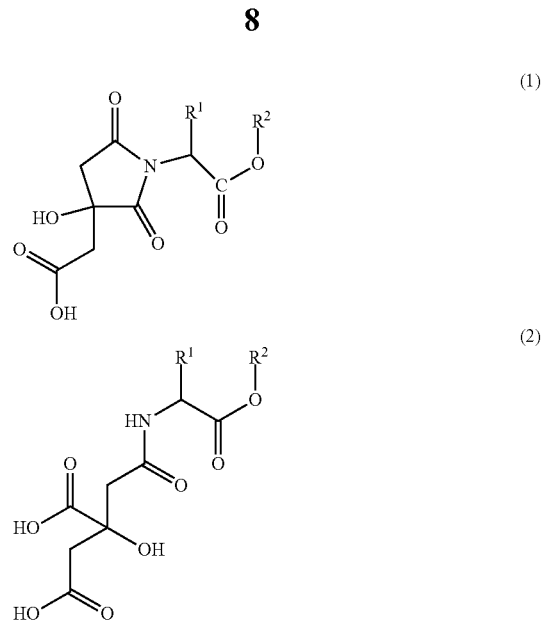

In the formulas, R¹ represents a C1 to C3 alkyl group optionally having a carboxyl group or a hydroxyl group and R² represents a hydrogen atom, or R¹ and R² optionally form a cyclic structure together to represent a C2 to C3 alkylene chain.

The C1 to C3 alkyl group in the aforementioned C1 to C3 alkyl group optionally having a carboxyl group or a hydroxyl group is a linear or branched alkyl group having 1 to 3 carbon atoms, specifically, examples thereof can include a methyl group, an ethyl group, a n-propyl group, and an isopropyl group. Further, the C1 to C3 alkyl group having a carboxyl group is represented by the following formulas.

The aforementioned C1 to C3 alkyl group having a carboxyl group is represented by the following formulas:

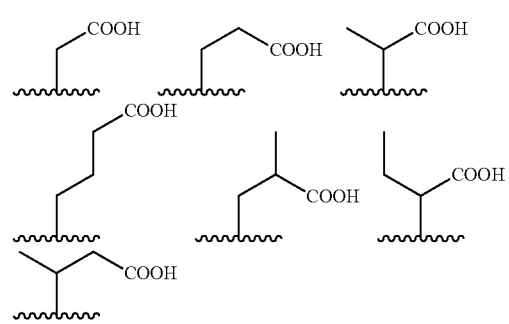

(wherein each wavy line represents a binding position to the adjacent carbon atom).

The aforementioned C1 to C3 alkyl group having a hydroxyl group is represented by the following formulas:

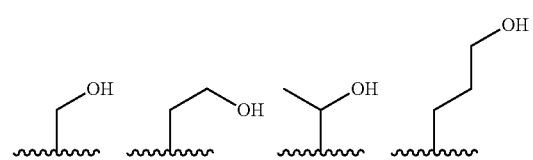

-continued

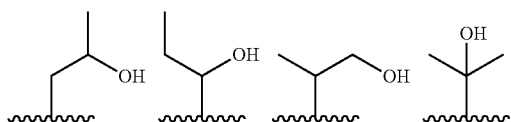

(wherein each wavy line represents a binding position to the adjacent carbon atom).

$R^1$ and $R^2$ may form a cyclic structure together, and the cyclic structure is a cyclic structure in which the hydroxyl group in the C2 to C3 alkyl group ($R^1$) having a hydroxyl group is dehydrated and condensed with a carboxyl group having $R^2$. The aforementioned cyclic structure is, for example, represented by the following formulas:

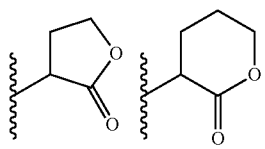

(wherein each wavy line represents a binding position to the adjacent nitrogen atom).

Specifically, examples of the compound represented by formula (1) can include the compounds shown below.

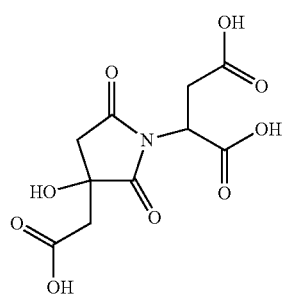

I

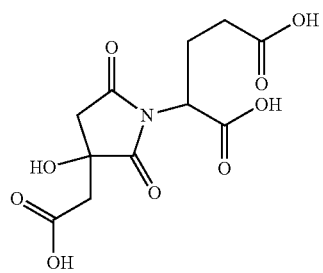

III

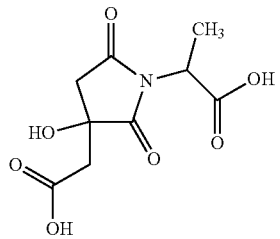

IV

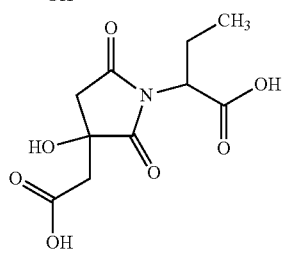

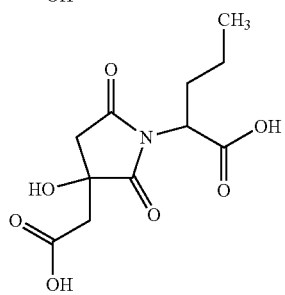

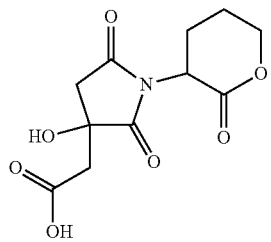

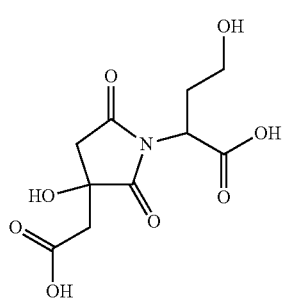

Among the aforementioned compounds, compound I is preferable.

Specifically, examples of the compound represented by formula (2) can include the compounds shown below.

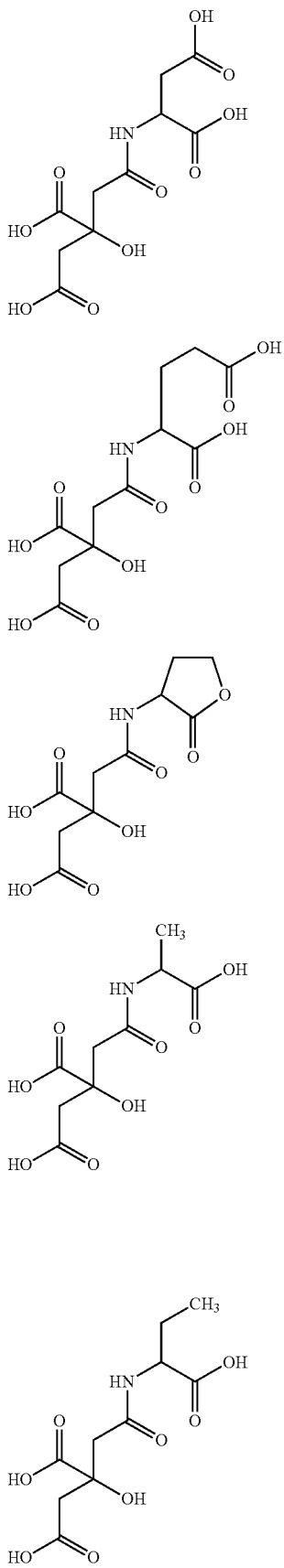

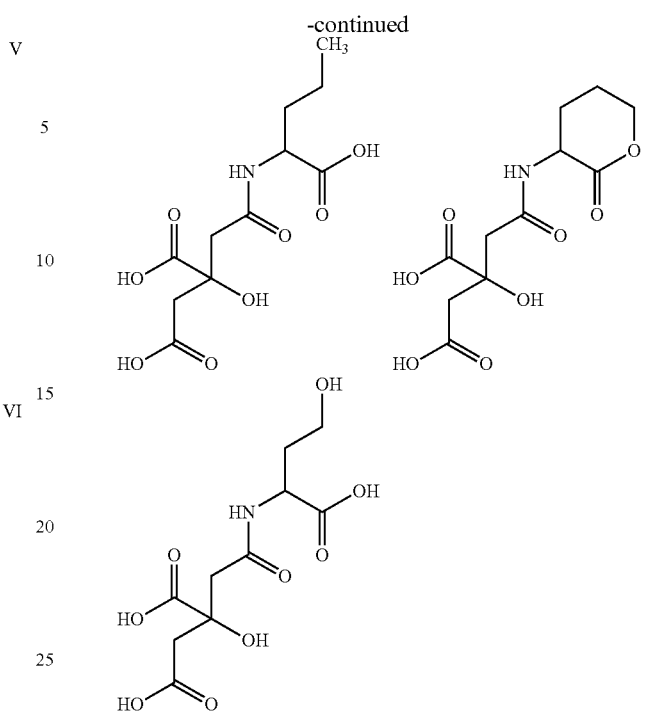

Among the aforementioned compounds, compound V is preferable.

The compounds of the present invention include the form of salts, and examples of the salts can include a metal salt produced from aluminum, calcium, lithium, magnesium, potassium, sodium, and zinc, and an organic salt produced from N,N'-dibenzylethylenediamine, chloroprocaine, choline, diethanolamine, ethylenediamine, N-methylglucamine, lysine, and procaine. The compounds of the present invention contain a plurality of carboxyl groups, where any one or more of the carboxyl groups may be in the form of salts.

The compound represented by formula (1) has an asymmetric carbon atom, where such a compound includes all possible optical isomers, and these optical isomers can be used at any ratio. For example, an optically active compound may be an enantiomer, a racemic compound, or a mixture of enantiomers at any ratio, or may be a mixture of diastereomers at any ratio when two or more asymmetric points are present. However, when it is produced using a raw material derived from a natural product, an amino group derived from L-amino acid is contained in the structure, and therefore a structure having the same configuration as L-amino acid with respect to the asymmetric carbon to which a nitrogen atom is bound (a mixture of diastereomers derived from the asymmetric carbon to which the hydroxyl group of citric acid is bound) is obtained. The present invention includes all of these compounds and mixtures.

(Liver Disorder Inhibitor)

The compound represented by formula (1) and the compound represented by formula (2) below show actions of reducing AST and ALT in blood when administered to rats and thus can used as liver disorder inhibitors. The measured values of AST and ALT in blood are indices which increase depending on the degree of disorder in liver tissue, and therefore measured values deviating from the ranges of normal values (reference values) (for example, AST is 12 to 40 IU/L, and ALT is 5 to 40 IU/L) indicate that any disease having disorders is present in liver tissue. The liver disorder inhibitor of the present invention has not only a therapeutic effect for liver disorder to cure a patient with liver disorder and a therapeutic effect to accelerate healing by preventing progression of sustained liver disorder of a patient with liver disorder but also an inhibitory effect against liver disorder to prevent healthy people from developing liver disorder. In the present invention, liver disorder means various liver dysfunctions, and examples thereof include acute hepatitis, chronic hepatitis, fatty liver, hepatitis A, hepatitis B, hepatitis C, cholestatic liver disorder, liver failure, alcoholic liver disorder, NASH (Non-alcoholic steatohepatitis), drug-induced liver disorder, and autoimmune liver disorder.

(Use as Foods)

Further, focusing on the fact that the compound represented by formula (1) and the compound represented by formula (2) below have not only a therapeutic effect for liver disorder to cure a patient with liver disorder and a therapeutic effect to promote healing by preventing progression of sustained liver disorder of a patient with liver disorder but also an inhibitory effect against liver disorder to prevent healthy people from developing liver disorder, these compounds can be used as food products or food additives. That is, examples thereof include a functional food product, a food product for specified health use, a healthy food product, a food material, and a food additive which contain one or more of the compound represented by formula (1) and the compound represented by formula (2).

For example, after a suitable aid such as rice flour, oil and fat, starch, lactose, malt sugar, vegetable fat and oil powder, cacao fat powder, and stearic acid is added to one or more of the compound represented by formula (1) and the compound represented by formula (2), the mixture may be formed into an edible form such as a paste, a drink, a soft capsule, a seamless capsule, a hard capsule, granules, and a pill using a conventional method, so as to be eaten, or may be added to various foods such as a bread including a plain bread and a sweet bread; a jam; a biscuit; a cookie; a confectionery including a rice cracker; a cake; a gum; an instant food including an instant noodle, an instant miso soup, and an instant soup; an ice cream product; a beverage including yogurt, milk, a drink agent, and a soft drink (such as tea, coffee, black tea, and juice) for use. The amount of the one or more of the compound represented by formula (1) and the compound represented by formula (2) of the present invention mixed is appropriately set depending on the type and state of the edible composition.

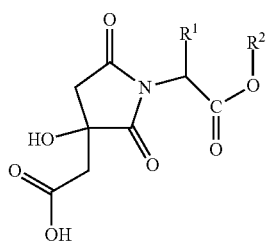

(1)

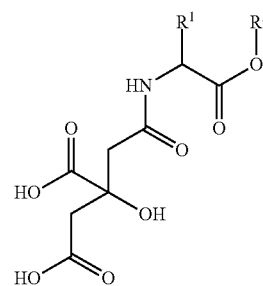

(2)

In the formulas, $R^1$ represents a C1 to C3 alkyl group optionally having a carboxyl group or a hydroxyl group and $R^2$ represents a hydrogen atom, or $R^1$ and $R^2$ optionally form a cyclic structure together to represent a C2 to C3 alkylene chain. In the present invention, the sentence, $R^1$ represents a C1 to C3 alkyl group optionally having a carboxyl group or a hydroxyl group, means any one of cases (1) to (3) below.

(1) $R^1$ is a C1 to C3 alkyl group having no substituent.

(2) $R^1$ is a C1 to C3 alkyl group having a carboxyl group. Examples of $R^1$ representing a C1 to C3 alkyl group having a carboxyl group specifically include a C1 alkyl group having a carboxyl group (that is, a methyl group having a carboxyl group), a C2 alkyl group having a carboxyl group (that is, an ethyl group having a carboxyl group), a C3 alkyl group having a carboxyl group (that is, a n-propyl group or an isopropyl group having a carboxyl group), a C1 to C2 alkyl group having a carboxyl group, and a C2 to C3 alkyl group having a carboxyl group.

(3) $R^1$ is a C1 to C3 alkyl group having a hydroxyl group. Examples of $R^1$ representing a C1 to C3 alkyl group having a hydroxyl group specifically include a C1 alkyl group having a hydroxyl group (that is, a methyl group having a hydroxyl group), a C2 alkyl group having a hydroxyl group (that is, an ethyl group having a hydroxyl group), a C3 alkyl group having a hydroxyl group (that is, a n-propyl group or an isopropyl group having a hydroxyl group), a C1 to C2 alkyl group having a hydroxyl group, and a C2 to C3 alkyl group having a hydroxyl group.

The C1 to C3 alkyl group in the C1 to C3 alkyl group optionally having a carboxyl group or a hydroxyl group is a linear or branched alkyl group having 1 to 3 carbon atoms, and examples thereof specifically include a methyl group, an ethyl group, a n-propyl group, and an isopropyl group. Further, the C1 to C3 alkyl group having a carboxyl group is represented by the following formulas.

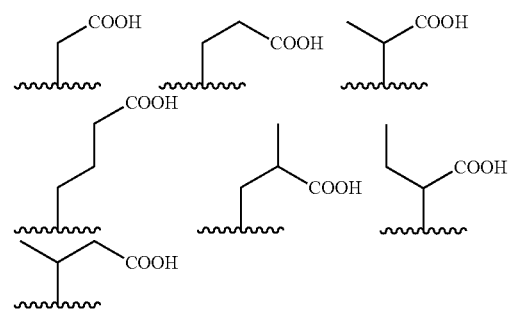

(wherein each wavy line represents a binding position to the adjacent carbon atom).

The C1 to C3 alkyl group having a hydroxyl group is represented by the following formulas.

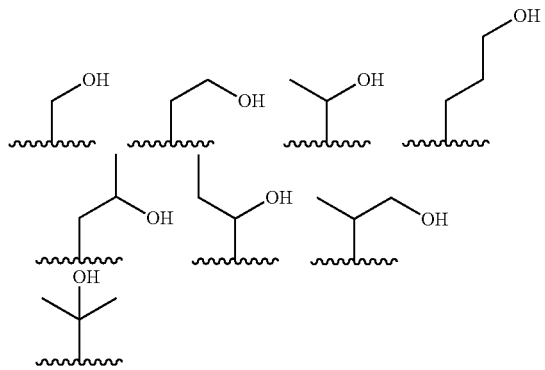

(wherein each wavy line represents a binding position to the adjacent carbon atom).

When $R^1$ and $R^2$ form a cyclic structure together, examples of the cyclic structure can include the same cyclic structure as in formula (1).

The liver disorder inhibitor of the present invention is not particularly limited as long as it contains a compound represented by formula (1) and/or a compound represented by formula (2). Further, a compound represented by formula (1) and/or a compound represented by formula (2) contained in the liver function improver may be provided in isolated form, but the form of a fraction containing compounds I and V obtained by extraction and the form of a concentrate (roughly purified solution) after a reaction solution obtained by synthesis is concentrated as needed are also included in the forms to provide the compounds.

The liver disorder inhibitor of the present invention may contain a pharmaceutically acceptable carrier which is widely used in the field of chemical production. Examples of the pharmaceutically acceptable carrier include the following pharmaceutical agents: a solvent (such as water, common normal saline, a buffer, glycerin, an organic solvent), an emulsifier, a suspending agent, a disintegrant, a binder, an excipient, a stabilizer, a preservative, a lubricant, an absorption delaying agent, and a liposome. Further, the liver disorder inhibitor can be prescribed in a dosage form suitable for parenteral administration, local administration, or oral administration. Such a dosage form is not particularly limited, and examples thereof include a tablet, a lozenge, a pill, a capsule, injection (for example, a sterile water solution or a dispersion), and sterile powder.

The effective dose of the liver disorder inhibitor of the present invention is in the range of 2.5 mg to 32000 mg/day, preferably in the range of 3 mg to 600 mg/day (adult), as the amount of the one or more compounds represented by formulas (1) and (2) contained in the liver disorder inhibitor.

(Extraction of Compounds)

Particularly when the compound represented by formula (1) of the present invention is compounds I and V, the compounds can be obtained by extraction, derivation, and isolation from ume extract. Specifically, the compounds can be obtained by the following procedure.

First, a wild species of ume having ume DNA only is crushed and squeezed, and the obtained juice is concentrated by heating to obtain a concentrate of the ume juice. Then, an appropriate amount of water is added to the concentrate, followed by removal of precipitate by centrifugation, to obtain supernatant 1. Subsequently, supernatant 1 is neutralized by adding a base such as sodium hydroxide and potassium hydroxide, and thereafter calcium chloride is added thereto for removing citric acid, malic acid, pectin, or the like contained in the supernatant, thereby generating calcium salts of citric acid, malic acid, pectin, or the like, followed by centrifugation so that the calcium salts precipitate, to obtain supernatant 2. Further, a base such as sodium hydroxide and potassium hydroxide is added to supernatant 2 to adjust the pH to 5.0 to 7.0, and ethanol is added thereto to perform ethanol precipitation reaction. The mixture containing ethanol is centrifuged to separate it into supernatant (ethanol-soluble fraction) and precipitate (ethanol-insoluble fraction), and an ethanol solution is added to the precipitate again, followed by centrifugation in the same manner, to obtain a precipitate.

A mixture obtained by adding purified water to the aforementioned precipitate is passed through a 1-kD to 100-kD ultrafiltration membrane, thereby removing macromolecular components, to obtain a filtrate containing low molecular-weight components. An ethanol solution is added to the aforementioned filtrate, followed by centrifugation to obtain a precipitate, and purified water is added to the precipitate, to remove insoluble matter such as calcium malate salt. The solution from which insoluble matter has been removed is concentrated by an evaporator, to obtain a fraction containing compounds I and V. Such a fraction can be used also as a composition containing compounds I and V, as it is. Thereafter, further concentration and known purification such as column chromatography are appropriately performed, so that compounds I and V can be obtained.

(Synthesis of Compound)

The compound represented by formula (1) can be obtained by dehydration condensation reaction of citric acid with an amine compound represented by formula (3), as shown below.

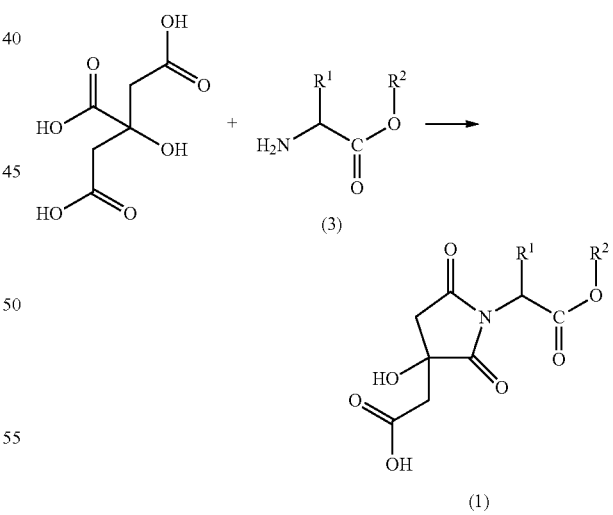

(in formula (1) and formula (3), $R^1$ and $R^2$ are as defined above).

In the dehydration condensation reaction of citric acid with the amine compound represented by formula (3), a mixture of citric acid and the amine compound represented by formula (3) is heated in a water bath at 80 to 100° C. to dissolve the amine compound represented by formula (3) therein and thereafter is reacted at 100 to 130° C., preferably at 115 to 125° C., for 30 minutes to 300 minutes, preferably 120 minutes to 240 minutes, so that the compound represented by formula (1) can be obtained.

Further, the ratio between the citric acid and the amine compound represented by formula (3) mixed (concentration of the citric acid:concentration of the amine compound represented by formula (3)) may be any value in the range of 75:1 to 12:10, and examples of the range include 50:1 to 20:10, 40:1 to 15:8, and 25:1 to 10:5. The concentration herein means a molar amount per unit volume (such as mol/L, mmol/L, mmol/ml, µmol/L, and µmol/mL). An example is to add and mix the amine compound represented by formula (3) having a final concentration of 10 to 120 mg/mL to a 250 to 750 mg/mL (1.19 mol/L to 3.57 mol/L) citric acid solution. Another example is to add and mix, when synthesizing compound I, aspartic acid corresponding to a final concentration of 10 to 20 mg/mL (75 mmol/L to 150 mmol/L) and asparagine corresponding to a final concentration of 80 to 120 mg/mL (533 mmol/L to 800 mmol/L) to a 250 to 750 mg/mL (1.19 mol/L to 3.57 mol/L) citric acid solution. In the case of individually adding aspartic acid with a final concentration of 10 to 120 mg/mL (75 mmol/L to 800 mmol/L) to the citric acid solution, 20 mg/mL or more of aspartic acid is not completely dissolved at the start of the reaction. However, aspartic acid is gradually dissolved therein with the progress of reaction by performing the reaction under stirring the mixed suspension, and finally the same title compound can be obtained. Since asparagine has high water solubility as compared with aspartic acid, asparagine having the same concentration can be dissolved in the citric acid solution at the start of reaction.

In the case of synthesizing cyclic compound I or II by this reaction, the synthesis can be achieved also using asparagine or glutamine, other than the amine compound represented by formula (3). Further, an autoclave can be used for this reaction.

In a method for synthesizing the compound represented by formula (1) by heating and reacting citric acid and the amine compound represented by formula (3), two carboxyl groups bound to the 1-position carbon (or the 3-position carbon) and the 2-position carbon of a propane chain which is a carbon chain skeleton of citric acid (IUPAC name: 2-hydroxypropane-1,2,3-tricarboxylic acid) form an imide bond with an amino group, thereby causing condensation and cyclization, to form a cyclic imide compound. The 1-position carbon and the 3-position carbon of citric acid are chemically equivalent carbons, but at the time when binding has occurred in any one of the carboxyl groups, a stereoisomer is formed with the 2-position carbon serving as an asymmetric carbon, and in the case of using L-amino acid or D-amino acid as the amine compound represented by formula (3), a diastereomer is formed.

In the case of using a solvent in the aforementioned organic reaction, the obtained reaction solution is concentrated, as needed, and thereafter the concentrate may be used as it is or may be used after appropriate post-treatment as the compound represented by formula (1). Specific examples of the method of post-treatment can include extraction and/or crystallization, and known purification such as chromatography.

The compound represented by formula (2) can be obtained as follows, by partial hydrolysis of the imide bond of the compound represented by formula (1) which has been synthesized from citric acid and the amine compound represented by formula (3) by the aforementioned method:

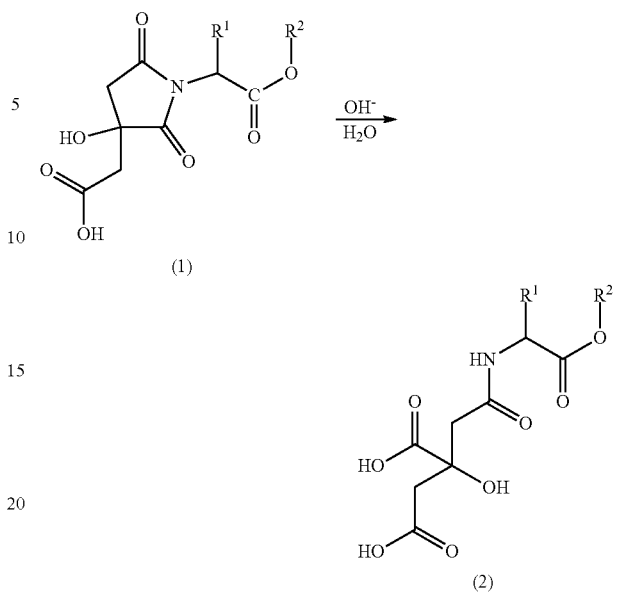

(in formula (1) and formula (2), $R^1$ and $R^2$ are as defined above).

As a method for converting the cyclic imide compound represented by formula (1) into the amide compound represented by formula (2), an aqueous solution of the cyclic imide compound represented by formula (1) is heated with a base, thereby opening the ring of the imide bond by hydrolysis, to obtain the amide compound. Examples of the aforementioned basic conditions include pH 6.0 or more, preferably pH 8.6 or more, further preferably pH 9.6 to pH 12.0, and examples of the base which is suitably used can include sodium hydroxide and potassium hydroxide which generate hydroxide ions in water. The heating conditions are 90° C. to 130° C. and 20 minutes to 240 minutes.

The duration and conditions of heating can be appropriately adjusted depending on the concentration of the object to be decomposed and the pH of the reaction solution, but heating at 121° C. for 20 to 60 minutes is preferable in the condition of pH 9.6 to pH 12.0. Further, an autoclave can be used for this reaction.

The aforementioned ring opening reaction is a reaction depending on the pH and therefore, after the synthesis of the compound represented by formula (1) by the aforementioned method, the ring opening reaction can be performed continuously by using the reaction mixture solution as it is and adjusting the pH by adding a base. Further, even in the case of purifying the compound represented by formula (1) by the aforementioned method, the reaction can be performed similarly by dissolving the purified product in water and thereafter adding a base thereto to adjust the pH.

Further, an autoclave can be used for this reaction.

Also in the ring-opened product of this reaction, the stereoisomer with the 2-position carbon of the propane chain of citric acid serving as the asymmetric center is maintained, and a diastereomer is formed in the case of using L-amino acid or D-amino acid as the amine compound represented by formula (3). Further, a compound represented by formula (4) below which is a structural isomer of the amide compound represented by formula (2) is produced as a side reaction product together with the amide compound represented by formula (2), but the amount thereof is limited, as compared with the amide compound represented by formula (2). In the compound represented by formula (4), no asymmetric carbon is generated from the carbon derived from citric acid:

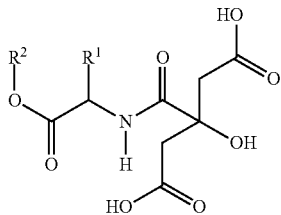

(4)

(in formula (4), $R^1$ and $R^2$ are as defined above).

Specifically, examples of the compound represented by formula (4) can include the compounds shown below.

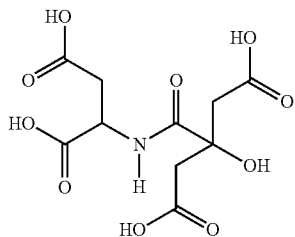

IX

In the case of using a solvent in the aforementioned organic reaction, after the obtained reaction solution is concentrated, as needed, the concentrate may be used as it is or may be used as the compound represented by formula (2) after appropriate post-treatment. Specific examples of the method of post-treatment can include extraction and/or crystallization, and known purification such as chromatography.

EXAMPLES

Hereinafter, the present invention will be described specifically by way of examples, but the present invention is not limited by these examples at all.

1. Separation and Purification of Active Components

First, a liquid concentrate of ume extract was prepared. A wild species of ume (cultivar: Shirakaga) having ume DNA only was crushed and squeezed, and the obtained juice was concentrated by heating to obtain a concentrate of the ume juice (ume extract).

In order to analyze water-soluble components contained in the ume extract, 1 g of the concentrate was diluted with 39 g of a 3 mM sulfuric acid solution (mobile phase of HPLC) (40-fold dilution), followed by removal of insoluble matter using a membrane filter, to obtain a diluted solution. FIG. 1 shows a chromatogram of the diluted solution by high-performance liquid chromatography (HPLC). The HPLC analysis conditions were as follows. The target component considered to be an active component in the chromatogram shows the peak at RT 21.1.

[Analysis System of HPLC]

Equipment: High performance liquid chromatograph, manufactured by JASCO Corporation Columns: Two coupled columns, Excelpak CHA-E11 (300 mm×4.6 mm, I.D., Yokogawa analytical systems Inc.)

Mobile phase: 3 mM sulfuric acid solution
Flow rate: 0.5 mL/min
Column temperature: 55° C.
Injection volume: 20 μL
Detection wavelength: 210 nm Then, a fraction containing the active component was prepared. Eight hundred (800) mL of water was added to 400 g of the aforementioned concentrate, followed by removal of the precipitate by centrifugation, to obtain supernatant 1. Subsequently, a sodium hydroxide aqueous solution (40 g/100 mL) was added to supernatant 1 in small amounts, thereby neutralizing the supernatant to adjust the acid-base property to pH 6.8, and thereafter calcium chloride (225 g/400 mL) was added thereto in order to remove citric acid, malic acid, pectin, or the like, contained in the supernatant, to obtain a mixture. Calcium salts of citric acid, malic acid, pectin, or the like, were generated in the aforementioned mixture, and these salts were precipitated by centrifugation, to obtain supernatant 2. Further, a sodium hydroxide aqueous solution (40 g/100 mL) was added to supernatant 2 in small amounts to adjust the pH to 5.8 (to a fluid volume of 800 mL). Sixty (60) mL of ethanol was added per 40 mL of the aforementioned solution (to an ethanol concentration of 60%) for ethanol precipitation. The mixture containing a 60% ethanol solution was separated by centrifugation into supernatant (ethanol-soluble fraction) and precipitate (ethanol-insoluble fraction), and water was added to the precipitate to give 400 mL of a solution, followed by addition of ethanol (600 mL) again and centrifugation in the same manner, to obtain a precipitate.

Purified water was added to the aforementioned precipitate to give 400 mL of a solution, and the solution was passed through a 1-kD ultrafiltration membrane, thereby removing macromolecular components, to obtain a filtrate containing low molecular-weight components. Ethanol was added to the aforementioned filtrate to give a 60% ethanol solution, followed by centrifugation to obtain a precipitate, and 250 mL of purified water was added thereto to remove sparingly soluble substances in water such as calcium malate salt. The solution from which sparingly soluble matter was removed was concentrated by an evaporator, to obtain a concentrate containing readily soluble components in water. The components contained in the concentrate were analyzed by HPLC. FIG. 2 shows the HPLC chromatogram. The HPLC analysis conditions in FIG. 2 are the same as the HPLC analysis conditions in FIG. 1. In the concentrate, impurities derived from ume extract were partially removed, and the configuration ratio of the peak derived from the component considered to be an active component (at RT 21.1 minutes) increased, thereby achieving partial purification.

As a result of observation by enlarging the HPLC chromatogram of the fraction containing the active component, a bulge (shoulder peak) was observed on the left shoulder of the peak of the active component (at RT 21.1 minutes), and it was observed that the peak of a component having a slightly short retention time was overlapped. The component of the shoulder peak showed a retention time very close to that of the main peak of the active component and therefore was predicted to be observed for a relevant component, and the peak behavior with changes in acid-base property was investigated. As a result, it was observed that, when the acid-base property was adjusted to neutral to alkaline, followed by heating at 121° C. for 30 minutes, the component at RT 20.7 minutes corresponding to the position of the shoulder peak increased on the HPLC chromatogram. FIG.

3 shows the chromatogram of a sample obtained by heating part of the fraction containing the active component under alkali-added conditions.

The active component derived from ume extract (the component at RT 21.1 minutes in FIG. 3) and a component in which the active component was changed by alkali heating (the component at RT 20.7 minutes in FIG. 3: which will be hereinafter referred to as a derivative of the active component) were further purified from the fraction of the concentrate ([0053]) by preparative HPLC, and these components were analyzed by a HPLC evaluation system using columns having further excellent resolution. FIG. 4 shows the analysis results. As a result of using high-resolution columns, the active component (the component at RT 21.1 minutes in FIG. 3) initially observed as a single peak was divided into two peaks (peaks A and B in FIG. 4). Further, the derivative of the active substance (the component at RT 20.7 minutes in FIG. 3) was separated into three components (peaks C, D, and E in FIG. 4) as a result of using high-resolution columns. In the later-described analysis, it turned out that peak A and peak B were observed for compound I having a molecular weight of 289, and peaks C, D, and E were observed for compound V and compound IX having a molecular weight of 307.

The conditions for the HPLC analysis using high-resolution columns were as follows.

[HPLC Analysis System]
Equipment: Type 1200, manufactured by Agilent Technologies, Inc.
Columns: FLUOPHASE PFP (4.6×100 mm, 5 μm), manufactured by Thermo Fisher SCIENTIFIC
Mobile phase: A: 0.1% formic acid solution and B: acetonitrile, A/B=98/2
Flow rate: 0.8 mL/min
Column temperature: 35° C.
Injection volume: 10 μL
Detection wavelength: 200 nm 2. Synthesis and Structural Analysis of Compound I and Compound V The method for synthesizing compound I and compound V and the data of structural analysis are shown.

(Synthesis of compound I)

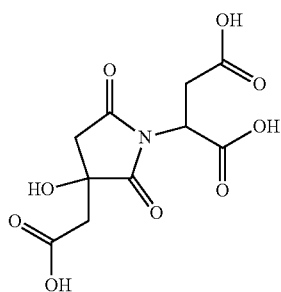

I

Water was added to 450 g of citric acid (monohydrate) (3.56 mol) to prepare 500 mL of a concentrated citric acid solution, and 60 g of L-asparagine (final concentration 0.667 mol/L) and 9 g of L-aspartic acid (final concentration 0.113 mol/L) were added to the solution, followed by dilution to give a fluid volume of 600 mL. The reaction solution was put into a pressure-resistant glass container and was sealed therein, followed by heating in a water bath at 90° C., to completely dissolve L-asparagine and L-aspartic acid added. Then, the reaction solution in the pressure-resistant container was put into an autoclave heated to about 80° C., followed by heating at 121° C. for 180 minutes.

After the reaction, the aforementioned reaction solution was naturally cooled to 25° C., and thereafter the reaction solution was taken out into a 5-L beaker, followed by cooling with ice. About 120 g of sodium hydroxide was dissolved in 500 mL of purified water to give a sodium hydroxide aqueous solution, followed by cooling with ice, and the sodium hydroxide aqueous solution was gradually added to the aforementioned reaction solution, to neutralize the reaction solution to pH 5.8 (the neutralization was performed with the temperature being checked to be 25° C. since heat of neutralization was generated). After the neutralization, the volume of the reaction solution was adjusted to 1200 mL using purified water. Then, 200 g of calcium chloride (dihydrate) was dissolved in 2 L of purified water, to prepare a calcium chloride solution, and about half the amount was added to the aforementioned reaction solution, followed by good stirring, and was allowed to stand still for about 16 hours. A white precipitate (calcium citrate) was formed in the solution. Since a new white precipitate settled out upon further adding the calcium chloride solution thereto, the calcium chloride solution was gradually added thereto, and about 2 L of the calcium chloride solution (1.36 mol as the amount of calcium chloride) was added to 1200 mL of the neutralized reaction solution. Purified water was added to the mixed solution to give a solution in a total amount of 3600 mL, and thereafter the white precipitate being citric acid calcium was removed by centrifugation, to collect a supernatant. Then, the supernatant was concentrated to 800 mL by an evaporator. Ethanol in an amount of 1860 mL was added to the concentrated aqueous solution, followed by stirring. After being allowed to stand still for a while, the mixed solution to which ethanol was added was separated into two layers of a comparatively transparent upper layer (ethanol layer) and a colored viscous lower layer solution. The solution was separated to collect the lower layer, followed by dilution with purified water to about 800 mL, and thereafter ethanol remaining in the solution was distilled off by an evaporator. As a result of HPLC analysis of an aqueous solution of the obtained lower layer (roughly purified solution I), a peak was observed at RT 21.1, and it was confirmed from the result that the same component as the active component extracted and separated from ume extract above was synthesized (FIG. 5). The active component turned out to be compound I by structural analysis, which will be described below.

The HPLC analysis conditions for the confirmation of the synthesized active component (FIG. 5) were as follows.

[Analysis System of HPLC]
Equipment: High performance liquid chromatograph, manufactured by JASCO Corporation
Columns: Two coupled columns, Excelpak CHA-E11 (300 mm×4.6 mm, I.D., Yokogawa analytical systems Inc.)
Mobile phase: 3 mM sulfuric acid solution
Flow rate: 0.5 mL/min
Column temperature: 55° C.
Injection volume: 20 μL
Detection wavelength: 210 nm

[Synthesis of Compound V]
Solutions with their acid-base property adjusted respectively to pH 7.6, pH 8.6, and pH 9.6 by adding sodium hydroxide to roughly purified solution I containing the active component synthesized above were prepared, followed by heating at 121° C. for 30 minutes. Each solution heated under alkaline conditions was analyzed by the same HPLC evaluation system as in synthesis and study of compound I, and changes in the peak at RT 21.1 minutes of compound I were observed. As a result, the peak at RT 21.1 minutes in the solution adjusted to pH 9.6 almost disappeared, and a new peak was observed at RT 20.7 (FIG. 6). The component at RT 20.7 minutes was consistent with the derivative of the active component obtained by hydrolysis, under alkali-added conditions, of the active component extracted and purified from ume extract above. It turned out from the later-described analysis that the peak of the derivative of the active component included mainly compound V and a small amount of compound IX. Compound IX is a structural isomer of compound V.

(Isolation and Structural Analysis of Compound I and Compound V Synthesized)

An alkali was added to roughly purified solution I produced by the aforementioned synthesis method to pH 6.5, followed by heating (at 121° C. for 30 minutes), to produce samples containing the active component (the component at RT 21.1 minutes) and the derivative of the active component (the component at RT 20.7 minutes), and their structural components were confirmed by HPLC analysis system using high-resolution columns. The results are shown in (FIG. 7). The component at RT 21.1 minutes was separated into two peaks, peak A and peak B in FIG. 7, and the retention time of these peaks was consistent with the retention time of peak A and peak B in FIG. 4 derived from the active component extracted and separated from ume extract. The component at RT 20.7 minutes was observed as three peaks at RT 2.9 to 3.5 minutes (peaks C, D, and E in FIG. 7). The retention time of these peaks in HPLC was consistent with the retention time of the peaks (peaks C, D, and E in FIG. 4) derived from the derivative of the active component extracted and separated from ume extract. It was confirmed from these results that the active component and the derivative thereof obtained by the aforementioned synthesis method were the same as the components contained in the ume extract.

(Isolation and Structural Analysis)

The active components separated and detected in the aforementioned analysis using high-resolution columns (peaks A and B in FIG. 7) and the derivatives of the active component (peaks C, D, and E in FIG. 7) were further purified by column chromatography. As a result, one component of the two peaks of the active component (peak B in FIG. 7, which will be hereinafter referred to as peak B) could be isolated. As a result of mass spectrometry of the component by LC-MS analysis system, structural analysis of the component by NMR, analysis of functional groups by IR, the component turned out to have the following structure expressed as compound I. The structural analysis was performed by specifying the chemical formula and basic skeleton by mass spectrometry and NMR spectroscopy, and denying acid anhydride (about 1800 $cm^{-1}$), and observing the spectrum (about 1700 $cm^{-1}$) considered to be derived from imide by IR spectrum. The compound had a structure in which an amino group of aspartic acid and two carboxyl groups of citric acid were condensed to form a cyclic imide.

The measurement conditions for NMR, LC-MS, and IR used for the structural analysis of compound I were as follows.

[Analysis System of NMR]
Equipment: AVANCE type 500 (cryo Probe), manufactured by Bruker Biospin
Measured nuclides: Hydrogen ($^1H$) and carbon ($^{13}C$)
Measurement solvent: $D_2O$
Measurement method: $^1H$ NMR, $^{13}C$ NMR, $^{13}C$ NMR (DEPT), $^1H$-$^1H$ COSY, HMQC, and HMBC

[Analysis System of LC-MS]
Liquid chromatographer
Equipment: Type 1200, manufactured by Agilent Technologies, Inc.
Columns: FLUOPHASE PFP (4.6×100 mm, 5 μm), manufactured by Thermo Fisher SCIENTIFIC
Mobile phase: A: 0.1% formic acid solution and B: acetonitrile, A/B=98/2
Flow rate: 0.8 mL/min
Column temperature: 35° C.
Injection volume: 10 μL
Detection wavelength: 200 nm
Mass spectrometer
Equipment: Type 6140, manufactured by Agilent Technologies, Inc.
Measurement mode: Positive mode and Negative mode
Measurement mass range: m/z 50 to 1350

[Analysis System of FT-IR]
Equipment: Cary 670, manufactured by Agilent Technologies, Inc. Measurement method: ATR microscopy
Measurement range: 700 $cm^{-1}$ to 4000 $cm^1$
Resolution: 4 $cm^{-1}$
The cumulative number of times: 64 times
Crystal: Germanium

[Data of Peak B]
NMR data
$^1H$ NMR (500 MHz, $D_2O$) δ=2.89, 2.90, 2.99, 3.19, 3.22, and 5.02;
$^{13}C$ NMR (125 MHz, $D_2O$) δ=36.798, 43.990, 44.557, 53.739, 74.963, 176.172, 176.908, 178.084, 179.376, and 182.172;
Mass Spectral Data
LC-MS m/z: 290 $(M+H)^+$ and 288 $(M-H)^-$ (at RT 4.0 minutes)
FT-IR Data
1704.8 $cm^{-1}$, very strong

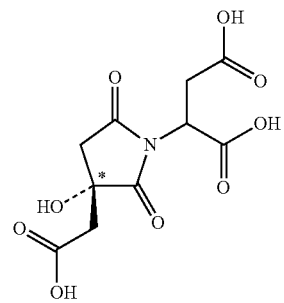

I(a)

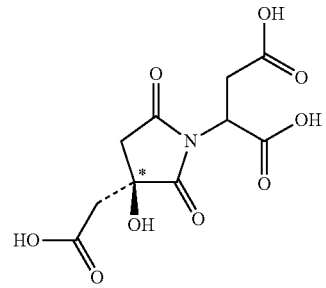

I(b)

(In the formulas, each symbol * represents the position of an asymmetric carbon in a structure derived from citric acid. Further, the dashed line indicates the presence on the back side of the plane, and the thick line indicates the presence on the front side of the plane.)

In compound I, diastereomers with the 2-position carbon (carbon with symbol * attached) of a propane chain derived from citric acid serving as an asymmetric carbon are present (although an asymmetric carbon is present also in a structure derived from aspartic acid, almost no enantiomer is present therein in the case of using a ume which is a natural plant material as a raw material since an amino acid almost in L-form serves as a raw material). Supposing that the diastereomers are diastereomers I(a) and I(b), the active component (peak B) isolated above is observed for either diastereomer I(a) or I(b), and the NMR analysis data of compound I shown above is the data of either I(a) or I(b). The diastereomer to which isolated peak B corresponds cannot be distinguished from the results obtained. It can be confirmed that, of two peaks derived from the active components shown in FIG. 4 and FIG. 7, peak A (which will be hereinafter referred to as peak A) is observed for the diastereomer of isolated peak B, from the facts that their molecular weights were consistent with each other, and their NMR data showed similar spectrum patterns very close to each other. Then, mass spectrometry by LC-MS and spectrum analysis by NMR were performed on a sample with abundant peak A (with slight incorporation of peak B) in the same manner. The results of mass spectrometry showed that the molecular weights of both peak A and peak B were 289 to be consistent with each other, and it was also confirmed that the NMR spectrum data showed similar spectrum patterns close to each other. Accordingly, it was confirmed that peak A and peak B purified as the active substances were diastereomers having the structure of compound I.

[Data of Peak A]
NMR Data
$^1$H NMR (500 MHz, $D_2O$) δ=2.90, 2.96, 3.05, 3.25, 3.28, and 5.15;
$^{13}$C NMR (125 MHz, $D_2O$) δ=36.129, 43.290, 44.400, 52.779, 75.201, 174.774, 175.865, 177.187, 179.214, and 181.755;
Mass Spectral Data
LC-MS m/z: 290 $(M+H)^+$ and 288 $(M-H)^-$ (at RT 4.0 minutes)
FT-IR Data
1706.9 $cm^{-1}$, very strong

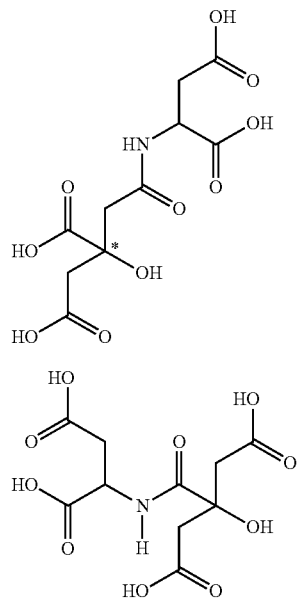

(In the formulas, symbol * represents the position of an asymmetric carbon in a structure derived from citric acid.)

As a result of the analysis using high-resolution columns, it could be confirmed that the derivative of the active component had a peak composed of three components ([0064]). As a result of analyzing these three components by LC-MS, it was confirmed that these three components had the same molecular weight (molecular weight: 307) and a structure in which one water molecule was added to the structure of compound I (molecular weight 289), and they were partial hydrolysates of compound I. As a result of further analyses such as NMR analysis, the presence of compound V and compound IX was confirmed.

These compounds are produced by opening the imide ring of compound I and are classified into two types of compound V and compound IX depending on the style of ring opening, where compound V is preferentially produced under alkali-added conditions. Diastereomers in which the 2-position carbon (carbon with symbol * attached) of the propane chain derived from citric acid serves as an asymmetric carbon are present in compound V, but these diastereomers cannot be distinguished from each other by NMR and LC-MS data. These diastereomers of compound V are obtained respectively as the hydrolysates of the diastereomers of compound I. Compound IX is produced in a small amount from hydrolysis of both diastereomers of compound I. Accordingly, the three components detected in the analysis of the derivative of the active component using high-resolution columns turned out to be two components of the diastereomers of the compound V, and compound IX.

The NMR data of compound V (data of one of the diastereomers) and the LC-MS data of a mixture of compound V and compound IX (though the three types were measured at the same time, a single result was obtained) are shown below. The analysis conditions were the same as in the analysis of compound I.

[NMR Data of Compound V]
$^1$H NMR (500 MHz, $D_2O$) δ=2.78, 2.88, 2.95, 3.05, and 4.75
$^{13}$C NMR (125 MHz, $D_2O$) δ=38.7, 46.1, 47.3, 52.1, 76.6, 166.5, 174.0, 176.9, 177.3, and 179.8
[Data of a Mixture of Compound V and Compound IX]
LC-MS m/z: 308 $(M+H)^+$, 330 $(M+Na)^+$, and 306 $(M-H)^-$ (at RT 2.8 to 3.5 minutes)

(Synthesis of compound II)

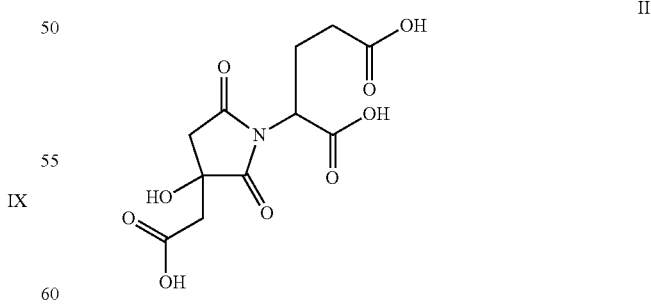

L-Glutamic acid was added to a 500 mg/mL citric acid (monohydrate) solution to a final concentration of 40 mg/mL (solubility limit at 90° C.), followed by complete dissolution in a water bath at 90° C. and thereafter heating at 121° C. for 240 minutes in an autoclave. As a result of analysis by HPLC evaluation system after the heating, as a result of HPLC analysis after the heating, peaks derived from components produced by the heating appeared at RT 5.8 and RT 11.5 (FIG. 8). As a result of LC-MS analysis, the molecular weight of the component at RT 5.8 minutes (peak 1 in FIG. 8) was 303, indicating that a compound in which citric acid was bound to an amino group of L-glutamic acid by an imide bond so as to form the same skeleton as that of compound I was synthesized. Further, the molecular weight of the component at RT 11.5 minutes (peak 2 in FIG. 8) was 129, and this value was consistent with the molecular weight of an L-glutamic acid anhydride cyclized by dehydration and condensation of a side chain and the main chain of L-glutamic acid.

The analysis conditions for HPLC analysis and LC-MS analysis used for the synthesis and study of compound II above were as follows.

[LC-MS Analysis System]
Liquid chromatographer
Equipment: ACQUITY UPLC, manufactured by Waters Corp.
Column: ULTRON PS-80H, manufactured by SHINWA CHEMICAL INDUSTRIES, LTD., (4.6×250 mm)
Mobile phase: 0.1% formic acid solution
Flow rate: 0.25 mL/min
Column temperature: 55° C.
Injection volume: 1 µL
Mass spectrometer
Equipment: Synapt G2-S, manufactured by Waters Corp.
Measurement mode: Positive mode and Negative mode
Measurement mass range: m/z 50 to 1000

[LC-MS Data of Synthesis Reaction Solution of Compound II]
LC-MS m/z: 304 (M+H)$^+$, 321 (M+NH$_4$)$^+$, 326 (M+Na)$^+$, 629 (2M+Na)$^+$, 302 (M–H)$^-$, and 605 (2M–H)$^-$ (at RT 5.8 minutes) LC-MS m/z: 130 (M+H)$^+$ and 128 (M–H)$^-$ (at RT 11.5 minutes)

Then, L-glutamine was added to a citric acid solution, followed by heating, in the same manner. The amount of L-glutamine added to the citric acid (500 mg/mL) solution was 70 mg/mL (solubility limit at 90° C.). After complete dissolution in a water bath at 90° C., it was heated at 121° C. for 240 minutes in an autoclave. As a result of analysis by the same HPLC evaluation system, peaks of products at the same retention time as in the case of using L-glutamic acid as a raw material were obtained in the solution after the heating. Accordingly, even in the case of using L-glutamine as a raw material instead of L-glutamic acid, compound II having the same structure is obtained.

(Synthesis of compound III)

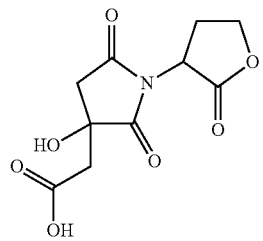

III (S)-α-Amino-γ-butyrolactone (alias (L)-homo-serine lactone) was added to a citric acid solution (500 mg/mL) to a final concentration of 100 mg/mL (solubility limit at 90° C.), followed by heating at 121° C. for 240 minutes in an autoclave. As a result of HPLC analysis after the heating, a peak derived from a component produced by the heating appeared at RT 7.9 minutes (FIG. 9). As a result of LC-MS analysis, the molecular weight of the component at RT 7.9 minutes was 257, indicating that a compound in which citric acid was bound to an amino group of (L)-homo-serine lactone by an imide bond so as to form the same skeleton as that of compound I was synthesized. The analysis conditions for HPLC analysis and LC-MS analysis used for the evaluation were the same as those in the evaluation of compound II.

LC-MS analysis data obtained in the synthesis and study of compound III above is shown below.
[Data of Compound III]
LC-MS m/z: 258 (M+H)$^+$, 275 (M+NH$_4$)$^+$, 280 (M+Na)$^+$, and 256 (M–H) (at RT 7.9 minutes)

(Synthesis of compound IV)

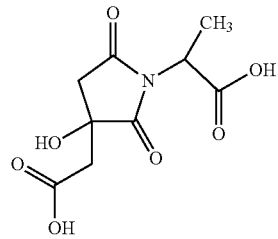

IV

L-Alanine was added to a citric acid (500 mg/mL) solution to a final concentration of 100 mg/mL (solubility limit at 90° C.), followed by heating at 121° C. for 240 minutes in an autoclave. As a result of HPLC analysis after the heating, a peak derived from a component produced by the heating appeared at RT 6.2 minutes (FIG. 10). As a result of LC-MS analysis, the molecular weight of the component at RT 6.2 minutes was 245, indicating that a compound in which citric acid was bound to an amino group of L-alanine by an imide bond so as to form the same skeleton as that of compound I was synthesized. The analysis conditions for HPLC analysis and LC-MS analysis used for the evaluation were the same as those in the evaluation of compound II.

LC-MS analysis data obtained in the synthesis and study of compound III above is shown below.
[Data of Compound IV]
LC-MS m/z: 246 (M+H)$^+$, 368 (M+Na)$^+$, 513 (2M+Na)$^+$, 244 (M–H)$^-$, and 489 (2M–H)$^-$ (at RT 6.2 minutes)

(Confirmation of Synthesis Method of Citric Acid and Amino Acid by Heating Being Selective Imide Formation Reaction)

(1) Comparison in Reaction Using Malic Acid

An aqueous solution of citric acid (250 mg/mL) and aspartic acid (11.1 mg/mL), and an aqueous solution of malic acid (250 mg/mL) and aspartic acid (11.1 mg/mL) each were heated at 121° C. for 30 minutes. As a result of HPLC analysis of the reaction solutions, a clear peak of compound I was observed in citric acid (see FIG. 11), but no clear peak was observed in malic acid (see FIG. 12). Also in an experiment carried out in the same manner, with aspartic acid being changed to asparagine, a clear peak of compound I as a single peak was observed in citric acid, but no clear peak was observed in malic acid. Further, also in an experiment carried out in the same manner, with citric acid and malic acid being mixed, only a synthesized compound derived from citric acid (RT: 21.1 minutes) was observed.

From above, it can be said that the imide formation reaction of an organic acid with an amino acid such as asparagine and aspartic acid selectively occurs only in citric acid.

(2) Comparison in Reaction Using Hydroxycitric Acid

Aspartic acid (15 mg/mL) and asparagine (100 mg/mL) were dissolved in a hydroxycitric acid solution (1.19 mol/L; the same molar concentration as 250 mg/mL of citric acid), followed by heating at 121° C. for 180 minutes. As a result of HPLC analysis of the reaction solution, at least three new peaks appeared as main new reaction products (see FIG. 13). In the case of reaction of hydroxycitric acid with an amino acid such as asparagine and aspartic acid, two types of imide compounds were assumed when the same imide formation reaction was simply performed, but actually three types of main new compounds were formed. This indicates that side reactions other than the imide formation reaction with an amino acid such as asparagine and aspartic acid (for example, amide formation reaction) have strongly occurred, and thus imide formation reaction is not selectively performed in hydroxycitric acid.

As described above, the selectivity of the reaction in which two carboxyl groups bound to adjacent carbons form an imide with an amino acid is lost, when a compound partially similar to citric acid such as malic acid and hydroxycitric acid is used as a raw material. Meanwhile, as seen in the synthesis and study of compound II, compound III, and compound IV above, the amino group for forming imide needs only to be an α amino group (a amino group bound to a carbon to which a carboxyl group is bound), the imide formation reaction is hardly affected by the structures of side chains, and the selectivity of imide formation is not lost.

3. Biological Activity Test

Test Example 1

(1) Preparation of Administration Products for Animal Test
(1) Preparation of Compound I Administration Product An 8 N sodium hydroxide aqueous solution was added dropwise to 100 mL of roughly purified solution I in small amounts, while checking the pH with a pH meter, to adjust the acid-base property of the solution to pH 6.5. Further, the mixture was diluted with a solvent.

(2) Preparation of Compound V Administration Product

An 8 N sodium hydroxide aqueous solution was added dropwise to 100 mL of roughly purified solution I in small amounts, while checking the pH with a pH meter, to adjust the acid-base property of the solution to pH 8.6, followed by heating at 121° C. for 30 minutes, and further the mixture was diluted with a solvent (the pH of the solution after the heating changed to about pH 6.2 due to acid formation by hydrolysis reaction).

Test on Liver Dysfunction Suppression Effect

The aforementioned administration products (1) and (2) were dissolved in a solvent composed of oligosaccharide, cyclic oligosaccharide, and D-sorbitol to give a solution, and the final concentration of compounds I and V dissolved in the solution administered was adjusted to 6 mg/mL. The solution in an amount of 6 g/kg as calculated from specific gravity of the solution was orally administered to 8 week-old Wistar male rats (CHARLES RIVER LABORATORIES JAPAN, INC.) for 7 days with free access to commercially available solid feed and tap water. The solvent free from the aforementioned compounds (1) and (2) in an amount of 6 g/kg was orally administered to the control animals for 7 days. On the 7th day after the start of administration, a 750 mg/kg dose of galactosamine hydrochloride (Wako Pure Chemical Industries, Ltd.) was intraperitoneally administered to each of the animals to which the control and compounds I and V were administered, and the abdomen was opened on the 9th day after the start of administration under pentobarbital anesthesia (50 mg/kg), to collect heparinized blood from the abdominal aorta. The obtained blood was separated into blood plasma, and the AST and ALT values thereof were measured by the JSCC standardization-corresponding method. In FIG. 14, the results are shown as average+standard deviation (the number of animals of each group was 20). Symbol * represents a significant difference ($p<0.05$) from the control group, which was tested by the Dunnett's test after the one-way analysis of variance.

FIG. 14 shows a graph showing changes in AST value (left) and ALT value (right) in blood plasma of rats. It turned out that, in the compound I administration group and the compound V administration group, the AST value and the ALT value were significantly low, that is, the liver disorder was treated and suppressed as compared with the control administration group.

Test Example 2

(Evaluation Test of Roughly Purified Compound I to NASH)
(1) Production of Roughly Purified Compound I Solution The concentration of compound I was determined from the peak intensity of the HPLC chromatogram so that the concentration of compound I contained was 26 mg/mL, to produce a roughly purified product from roughly purified solution I above. A solvent composed of oligosaccharide, cyclic oligosaccharide, and D-sorbitol was used as the solvent of the roughly purified compound I solution.

The pH of the final solution was adjusted to pH 6.0 using sodium hydroxide.

(2) Animal Experiment Procedure

Thirty (30) of C57BL/6J mice (manufactured by CHARLES RIVER LABORATORIES JAPAN, INC.) on the 17th day of pregnancy were individually bred with free access to gamma-irradiated solid feed (CRF-1, manufactured by Oriental Yeast Co., Ltd.) as standard diet and distilled water, and were allowed to give births. Offspring mice were divided into mice to which STZ was administered and mice without the administration (standard mice).

Twenty (20) μL of a 10 mg/mL (0.1M citric acid buffer with pH 4.5) solution of STZ (manufactured by Sigma-Aldrich) was subcutaneously administered to the back of each of the mice to which STZ was administered on the 2nd day after birth, with the date of birth counted as zero, using an insulin syringe (Myjector, manufactured by Terumo Corporation). After the STZ administration, the mice were bred by breastfeeding until they reach 4 weeks of age. After reaching 4 weeks of age, on the day after 4 weeks from the STZ administration, gender was determined, and male individuals were selected. The mice were weaned at this time and thereafter fed with high-fat diet (HFD32, manufactured by CLEA Japan, Inc.), to be bred as an STZ-induced NASH model mice group. The standard mice without the STZ administration were fed with CRF-1 instead of high-fat diet. Further, they were bred with free access to distilled water.

Venous blood of the male mice which reached 5 weeks of age was collected, after they were fasted 6 hours, by puncturing their tail vein, and blood sugar was measured using a simple blood glucose measurement device (Glutest Neo Sensor, manufactured by SANWA KAGAKU KENKYUSHO CO., LTD.). Further, their body weight was also measured on the same day.

Based on the body weight and blood sugar, the NASH model mice were grouped by stratified random assignment using a statistical analysis system EXSAS7.7 (manufactured by CAC EXICARE Corporation). The mice were divided into two groups of a roughly purified compound I group to which the roughly purified compound I solution was administered and a solvent group to which the solvent composed of oligosaccharide, cyclic oligosaccharide, and D-sorbitol, which was the control substance, was administered. Regarding the grouping date as the start date of administration, a 10 mL/kg (body weight) roughly purified compound I solution was administered to the roughly purified compound I group, and a 10 mL/kg (body weight) solvent was administered to the solvent group, using an oral gastric tube, once between 9 a.m. and 11 a.m. and once between 5 p.m. and 7 p.m., continuously for 14 days from the grouping date.

On the autopsy date after 14 days from the start of the administration test of the test substances, blood was collected from the abdominal vena cava of all the animals under somnopentyl anesthesia. After collecting the blood, the mice were euthanized by exsanguination. The obtained blood was immediately collected into a centrifuge tube in which heparin was put, followed by centrifugation at 3000 rpm for 10 minutes, to obtain blood plasma.

The aspartate transaminase (AST) concentration and the alanine transferase (ALT) concentration in blood plasma were measured by the JSCC standardization-corresponding method using an automatic analyzer, HITACHI 7180. The measured values were shown as average standard deviation (Mean±SD).

Results

The results are shown in FIG. 15. As is obvious from FIG. 15, as compared with the solvent group, the AST and ALT concentrations in blood plasma of the roughly purified compound I group each decreased. (Unpaired t-test (solvent group vs roughly purified compound I group), *p<0.05 vs solvent group, normal group (n=5), solvent group (n=19), roughly purified compound I group (n=15), AST: p=0.05, ALT: p<0.05)

INDUSTRIAL APPLICABILITY

In the test using the compounds of the present invention, AST and ALT in blood decreased. Accordingly, the compounds of the present invention can be used as liver disorder inhibitors.

The invention claimed is:

1. A compound represented by formula (1):

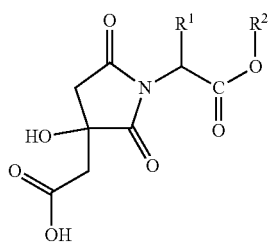

(1)

wherein $R^1$ represents a methyl group having a carboxyl group, and $R^2$ represents a hydrogen atom, or $R^1$ and $R^2$ optionally form a cyclic structure together to represent a C2 to C3 alkylene chain.

2. The compound according to claim 1, wherein the compound represented by formula (1) is represented by the following structures:

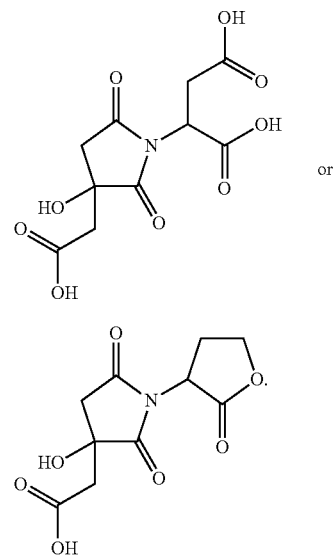

3. A method for inhibiting liver disorder comprising:
administering a compound represented by formula (1):

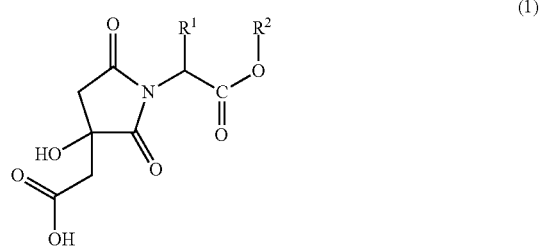

(1)

wherein $R^1$ represents a methyl group having a carboxyl group, and $R^2$ represents a hydrogen atom, or $R^1$ and $R^2$ optionally form a cyclic structure together to represent a C2 to C3 alkylene chain to a subject having liver disorder.

4. The method for inhibiting liver disorder according to claim 3, wherein the liver disorder is nonalcoholic steatohepatitis (NASH).

5. A method for synthesizing a compound represented by formula (1), comprising:
reacting by heating a mixture of citric acid and an amine compound represented by formula (3):

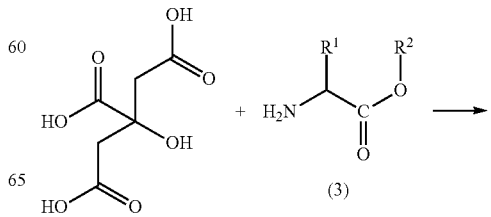

(3)

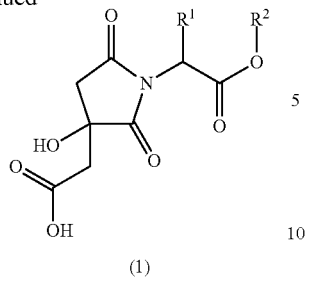

wherein R¹ represents a methyl group having a carboxyl group, and R² represents a hydrogen atom, or R¹ and R² optionally form a cyclic structure together to represent a C2 to C3 alkylene chain.

6. The method according to claim 5, wherein
the mixture of the citric acid and the amine compound represented by formula (3) is reacted at 100 to 130° C. for 30 minutes to 300 minutes.

7. The method according to claim 5, wherein
a mixing ratio of the citric acid to the amine compound represented by formula (3) (concentration of the citric acid:concentration of the amine compound represented by formula (3)) is 75:1 to 12:10.

* * * * *